United States Patent
Bova et al.

(10) Patent No.: US 10,413,610 B2
(45) Date of Patent: Sep. 17, 2019

(54) LIQUID FORMULATION

(71) Applicant: Luoda Pharma Pty Ltd, Caringbah (AU)

(72) Inventors: Nicholas Bova, Caringbah (AU); Stephen Page, Newtown (AU); Giuseppe Pippia, Chatswood West (AU)

(73) Assignee: LUODA PHARMA LIMITED, Dublin (IE)

( * ) Notice: Subject to any disclaimer, the term of this patent is extended or adjusted under 35 U.S.C. 154(b) by 0 days.

(21) Appl. No.: 15/725,798

(22) Filed: Oct. 5, 2017

(65) Prior Publication Data

US 2018/0028665 A1    Feb. 1, 2018

Related U.S. Application Data

(62) Division of application No. 14/401,943, filed as application No. PCT/AU2013/000522 on May 17, 2013, now Pat. No. 9,808,529.

(30) Foreign Application Priority Data

May 18, 2012 (AU) ................ 2012902062

(51) Int. Cl.
| | | |
|---|---|---|
| A61K 47/10 | (2017.01) | |
| A61K 9/08 | (2006.01) | |
| A61K 31/401 | (2006.01) | |
| A61K 45/06 | (2006.01) | |
| A61K 31/341 | (2006.01) | |
| A61K 31/497 | (2006.01) | |
| A61K 31/55 | (2006.01) | |
| A61K 31/40 | (2006.01) | |
| A61K 31/501 | (2006.01) | |

(52) U.S. Cl.
CPC .......... *A61K 47/10* (2013.01); *A61K 9/08* (2013.01); *A61K 31/341* (2013.01); *A61K 31/40* (2013.01); *A61K 31/401* (2013.01); *A61K 31/497* (2013.01); *A61K 31/501* (2013.01); *A61K 31/55* (2013.01); *A61K 45/06* (2013.01)

(58) Field of Classification Search
CPC ...... A61K 47/10; A61K 31/40; A61K 31/501; A61K 31/341; A61K 45/06; A61K 31/497; A61K 31/55; A61K 9/08; A61K 31/401
See application file for complete search history.

(56) References Cited

U.S. PATENT DOCUMENTS

| | | |
|---|---|---|
| 9,463,199 B2 | 10/2016 | Daemmgen et al. |
| 9,808,529 B2 | 11/2017 | Bova et al. |
| 2003/0170295 A1* | 9/2003 | Kim ............ A61K 9/7053 424/449 |
| 2004/0155338 A1 | 8/2004 | Kwan et al. |
| 2004/0157928 A1* | 8/2004 | Kim ............ A61K 9/4858 514/570 |
| 2006/0099230 A1 | 5/2006 | Chiang |
| 2007/0128239 A1 | 6/2007 | Hayes et al. |
| 2009/0048322 A1 | 2/2009 | Chow |
| 2012/0264694 A1* | 10/2012 | Boeren ............ A61K 31/44 514/16.3 |

FOREIGN PATENT DOCUMENTS

| | | |
|---|---|---|
| AU | 2010/201490 A1 | 11/2010 |
| EP | 1908469 A1 | 4/2008 |
| JP | 1993-262650 | 10/1993 |
| JP | 2006-514119 A | 4/2006 |
| JP | 2007-191419 A | 8/2007 |
| JP | 2007-529562 A | 10/2007 |
| JP | 2010-514778 A | 5/2010 |
| WO | WO-2004/071490 | 8/2004 |
| WO | WO-2004/091632 A1 | 10/2004 |
| WO | WO-2005/092343 A1 | 10/2005 |
| WO | WO-2005/117858 A2 | 12/2005 |
| WO | WO-2007/061529 A1 | 5/2007 |
| WO | WO-2008/082871 A1 | 7/2008 |
| WO | WO-2009/061529 A1 | 5/2009 |

OTHER PUBLICATIONS

"Inhibitors of the Renin-Angiotensin System", pp. 757-760 IN: Goodman and Gilman's the Pharmacological Basis of Therapeutics, Eighth Edition, Mc-Graw Hill, Inc., (1990).
Arora et al., ACE Inhibitors: A Comprehensive Review, Int. J. Pharm. Sci. Res., 4(2):532-49 (2013).
Chapter 2: Antihypertensive Drugs, IN: Alagarsamy, Textbook of Medicinal Chemistry, vol. 1, Elsevier Publishing (2010).
Dei Cas et al., Clinical pharmacology of inodilators. *J. Cardiovasc. Pharm.* 14(Suppl. 8): S60-71 (1989).
Haagstrom et al., Effect of pimobendan or benazepril hydrochloride on survival times in dogs with congestive heart failure caused by naturally occurring myxomatous mitral valve disease: the quest study. *J. Vet. Intern. Med.* 22(5): 1124-35 (2008).
International Search Report and Written Opinion of the International Searching Authority issued in connection withe International Application No. PCT/AU2013/000522, Australian Patent Office, dated Jul. 22, 2013.
Pollesello et al., Calcium sensitizers: What have we learned over the last 25 years, Int. J. Cardiol., 203:543-8 (2016).

(Continued)

*Primary Examiner* — Sudhakar Katakam
(74) *Attorney, Agent, or Firm* — Marshall, Gerstein & Borun LLP

(57) ABSTRACT

The invention relates to a liquid formulation comprising propylene glycol and an effective amount of an inodilator, an angiotensin converting enzyme inhibitor, or a combination of an inodilator and an angiotensin converting enzyme inhibitor and to use of the formulation for treating cardiac disease and/or hypertension.

11 Claims, 6 Drawing Sheets

(56) References Cited

OTHER PUBLICATIONS

Toutain et al., New insights on effect of kidney insufficiency on disposition of angiotensin converting enzyme inhibitors: case of enalapril and benazepril in dogs, *J. Pharmacol. Exp. Ther.* 292: 1094-103 (2000).

* cited by examiner

LIQUID FORMULATION

CROSS-REFERENCE TO RELATED APPLICATIONS

This Application is a Division of Application 14/401,943 filed on Nov. 18, 2014, which is a U.S. National Phase of PCT Application No. PCT/AU2013/000522, which claims priority to Australian Application No. 2012902062 filed on May 18, 2012. The entire contents of these applications are incorporated herein by reference in their entirety.

TECHNICAL FIELD

The present invention relates to a liquid formulation, in particular a liquid formulation comprising an inodilator, preferably pimobendan, and/or an angiotensin converting enzyme inhibitor, preferably enalapril or benazepril, for use in treating cardiac disease and/or hypertension in mammals, particularly dogs or cats.

BACKGROUND

Cardiac disease and/or hypertension are increasingly common problems in animals, particularly companion and zoo animals. For example, it is estimated that approximately 10% of domesticated dogs have cardiac disease. Common cardiac diseases in dogs include primary or secondary heart diseases, such as congestive heart failure (CHF), acute CHF, chronic CHF, decompensated endocardiosis (DCE), dilated cardiomyopathy (DCM), asymptomatic (occult) CHF, asymptomatic DCM, chronic valvular heart disease. Cardiac dysfunction can be associated with shock, gastric dilation, volvulus, and myocardial ischemia. Of these conditions, chronic valvular heart disease (CVHD) (also known as myxomatous valve degeneration) is one of the more common.

CVHD is more common in female than male dogs and commonly affects the left atrioventricular or mitral valve, although the right atrioventricular or tricuspid valve is involved in about 30% of cases. The prevalence of CVHD is much higher in small dogs, e.g. dogs weighing less than 20 kg, although larger dogs may also be affected. The cause of CVHD is unknown.

The American College of Veterinary Internal Medicine (ACVIM) published a consensus statement regarding CVHD in 2009 that sets out four stages for the functional classification of heart failure, namely:

Class I describes patients with asymptomatic heart disease;
Class II describes patients with heart disease that causes clinical signs only during strenuous exercise;
Class III describes patients with heart disease that causes clinical signs with routine daily activities or mild exercise; and
Class IV describes patients with heart disease that causes severe clinical signs even at rest.

The ACVIM consensus recommendations for treatment of CVHD include administration of an inodilator. The ACVIM has recommended twice daily administration of pimobendan, an inodilator, for the acute hospital based and chronic home based treatment of class III CVHD.

The ACVIM consensus recommendations also include treatment of chronic class Ill CVHD with furosemide, a diuretic, in addition to treatment with pimobendan. The diuretic is recommended for both acute and chronic treatment. For the acute treatment of CVHD the combination of furosemide, and pimobendan, is preferred.

The ACVIM consensus recommendations include the chronic treatment of CVHD with an angiotensin converting enzyme (ACE) inhibitor (ACE-I), such as enalapril. The evidence supporting ACE-I efficacy and safety is less clear for acute treatment of class Ill CVHD than for the chronic treatment of CVHD. Additionally, ACE-I's are useful in treatment of hypertension.

The preferred ACVIM consensus for chronic treatment of class III CVHD is administration of one or more of pimobendan, furosemide and an ACE-I.

In view of the significant problem of cardiac disease and/or hypertension there is a continuing need to develop improved formulations of active agents useful in the treatment of such conditions.

SUMMARY

In a first aspect, there is provided a liquid formulation comprising propylene glycol and an effective amount of an inodilator, an angiotensin converting enzyme inhibitor, or a combination of an inodilator and an angiotensin converting enzyme inhibitor.

In a second aspect, there is provided a liquid formulation comprising an effective amount of an inodilator and propylene glycol.

In a third aspect, there is provided a liquid formulation comprising an effective amount of an angiotensin converting enzyme inhibitor and propylene glycol.

In a fourth aspect, there is provided a liquid formulation comprising propylene glycol and an effective amount of a combination of an inodilator and an angiotensin converting enzyme inhibitor.

The formulation may comprise one or more further active agents, such as a diuretic or a calcium channel blocker.

In a fifth aspect, there is provided a method of treating cardiac disease and/or hypertension, comprising administering the formulation defined above to a subject in need thereof.

There is also provided use of propylene glycol and an effective amount of an inodilator, an angiotensin converting enzyme inhibitor or a combination of an inodilator and an angiotensin converting enzyme inhibitor, in the manufacture of a liquid formulation for the treatment of cardiac disease and/or hypertension.

There is also provided the formulation defined above for use in the treatment of cardiac disease and/or hypertension.

There is also provided use of a formulation defined above for treating cardiac disease and/or hypertension.

Cardiac disease includes primary and secondary heart disease. Primary heart disease may be selected from the group consisting of congestive heart failure (CHF), acute CHF, chronic CHF, decompensated endocardiosis (DCE), dilated cardiomyopathy (DCM), asymptomatic (occult) CHF, asymptomatic DCM, and chronic valvular heart disease, or a combination thereof. Secondary heart disease may be selected from the group consisting of cardiovascular dysfunction and impaired renal perfusion during anaesthesia, shock, gastric dilation, volvulus, myocardial ischaemia, and renal ischaemia, or a combination thereof.

Hypertension is commonly associated with activation of the renin-angiotensin-aldosterone system (RAAS). Disorders associated with hypertension include hyperadrenocorticism, hyperthyroidism, pheochromocytoma, primary hyperaldosteronism, diabetes mellitus, and renal disease, or a combination thereof.

In a sixth aspect, there is provided a process for the preparation of the formulation defined above which comprises mixing an effective amount of an inodilator and/or an angiotensin converting enzyme inhibitor with propylene glycol.

In a seventh aspect, there is provided a kit comprising a first formulation comprising an effective amount of an inodilator, and a second formulation comprising an effective amount of an angiotensin converting enzyme inhibitor, wherein the first and second formulations are held separately and at least one of the first and the second formulations comprises propylene glycol.

In an eighth aspect, there is provided a kit comprising a first formulation comprising an effective amount of an inodilator or an angiotensin converting enzyme inhibitor and a second formulation comprising a further active agent, wherein the first and second formulations are held separately and at least one of the first and the second formulations comprises propylene glycol.

DETAILED DESCRIPTION—LIQUID FORMULATION

Figure 1:
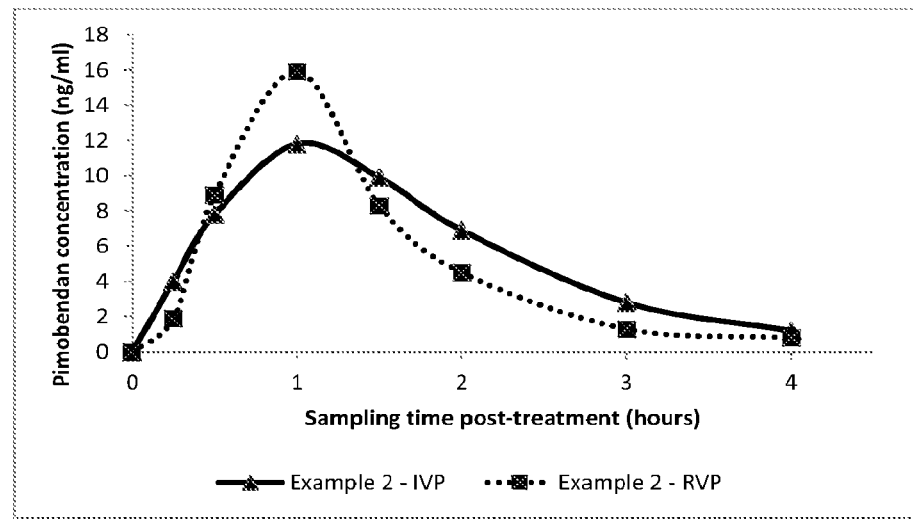
FIG. 1 is a graph which shows a comparison between plasma pimobendan concentrations in dogs after oral administration of an Investigational Veterinary Product IVP and a Reference Veterinary Product RVP.

One aspect provides a liquid formulation comprising propylene glycol and an effective amount of an inodilator, an angiotensin converting enzyme inhibitor, or a combination of an inodilator and an angiotensin converting enzyme inhibitor.

The formulation is suitable for oral or parenteral administration to a subject in need thereof, such as a dog or a cat, and can be used for acute or chronic treatment of a cardiac disease and/or hypertension. Oral administration is generally preferred for chronic therapy, while parenteral administration may be preferred for acute treatments. Thus, the liquid formulation may be in the form of a veterinary or human pharmaceutical formulation.

One aspect provides a liquid formulation comprising an effective amount of an inodilator and propylene glycol.

An example of an inodilator is pimobendan. Prior to the present invention pimobendan was available as an oral solid formulation or an injectable aqueous formulation. These formulations are often difficult to administer. This is particularly problematic for the treatment of chronic conditions, such as CVHD, as it is often necessary to administer the drug therapy for the remainder of the animal's life.

For example, administration of tablets to a dog or a cat is often challenging due to the subject's reluctance to swallow a tablet. Also, administration of drug therapy via injection, for example intravenous, intramuscular or subcutaneous injection routes, is difficult for animal owners that may not have any medical training, and may result in a number of possible complications. Furthermore, subjects that are difficult to dose are likely to become stressed by treatment and consequently the management of their clinical cardiac disease will be less than optimal. Also, if an animal is difficult to dose owners or carers will be reluctant to administer the treatment and compliance will be low, adding further to the less than optimal management of cardiac disease.

It has been surprisingly found that liquid formulations comprising an inodilator and propylene glycol have unexpectedly advantageous properties. In this regard, it has been found that a liquid formulation comprising pimobendan and propylene glycol provides a stable and orally bioavailable formulation.

Pimobendan is (RS)-6-[2-(4-methoxyphenyl)-1H-benzimidazol-5-yl]-5-methyl-4,5-dihydropyridazin-3(2H)-one and has the following structure:

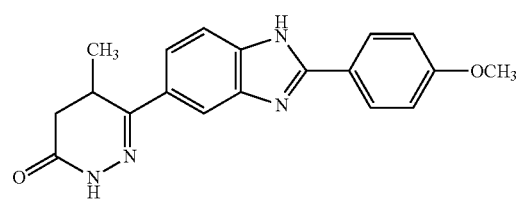 [SMILES: COc1ccc(-c2nc3cc(C4=NNC(=O)CC4C)ccc3[nH]2)cc1]

Pimobendan is a substituted benzimidazole which is highly insoluble in water. For example, 1 g of pimobendan dissolves in 10,000 mL of water. This solubility is known to be pH dependent, with solubility at pH 7 of 0.1 mg per 100 mL (or 1 g per 1,000,000 ml). These solubilities are too low to produce a solution with an effective amount of the drug. Further, while the pH of the subject's stomach is generally low, e.g. about pH 1 to 2 for canines, individual subject stomach pH may vary, e.g. a canine's stomach pH may vary between about pH 1 to about pH 8 which may be influenced by factors such as whether the pH measurement was taken during a fasted or fed state. Thus, prior to the present invention, the solubility of pimobendan in the stomach was known to be increased by the addition of citric acid to the administered formulation. Accordingly, in order to provide a bioavailable form of pimobendan, solid formulations of pimobendan were prepared comprising citric acid.

Alternatively, it has been shown that addition of increasing concentrations of hydroxypropyl-beta-cyclodextrin (HPβCD) to aqueous solutions of pimobendan can increase the solubility of pimobendan to concentrations of 0.5 to 1.5 mg/mL in an aqueous formulation at a pH greater than 5. However, at pH between 3 and 5, the addition of HPβCD does not effectively increase the aqueous solubility of pimobendan. Such aqueous formulations are useful for intravenous (IV) and/or subcutaneous (SC) administration of pimobendan.

Consequently, prior to the invention, it had been thought that additives such as citric acid or hydroxypropyl-beta-cyclodextrin were required to successfully prepare stable and bioavailable formulations of pimobendan, due to the low, and pH dependant, aqueous solubility of pimobendan.

As described herein, it has been found that liquid formulations of pimobendan can be prepared that are stable and are a source of readily and rapidly systemically absorbed or bioavailable pimobendan, while not requiring the addition of citric acid or hydroxypropyl-beta-cyclodextrin.

Liquid formulations have advantages over solid formulations when administering drugs to animals. For example, in most cases, it is easier to administer an active agent to an animal in a liquid form, by rapidly delivering a dose from, for example, a syringe or other dosing device, into the animal's mouth, not requiring the animal to chew or in some cases, swallow. Also, compared with tablets and capsules which contain a fixed dose, the quantity of the pimobendan to be administered can be readily adjusted according to the body weight of the subject by selecting the appropriate volume of the liquid formulation to administer.

The inventors surprisingly found that a stable solution of an inodilator, such as pimobendan, can be formed using propylene glycol without citric acid or a cyclodextrin. Unexpectedly, such a liquid formulation provides good solubility of pimobendan in aqueous solutions across a pH range consistent with in vivo pH levels. The inventors have also found that such liquid formulations provide orally bioavailable inodilator.

Citric acid produces a taste that is unpleasant to animals, such as dogs. Consequently, citric acid containing tablets have an unpleasant taste to dogs which is often not satisfactorily masked by the use of flavour enhancing substances. Accordingly, the finding that a stable formulation of pimobendan can be prepared using propylene glycol without citric acid has the advantage of providing formulations that are more palatable to animals, such as dogs or cats. This greatly improves the ease of administration of a pimobendan formulation to animals and may also assist in the long term maintenance of treatment.

The solubility of pimobendan in a formulation comprising HPβCD in water at a pH between 3 and 5 is low. Such a formulation may not be suitable for oral administration as pimobendan's aqueous solubility is not maintained over a broad pH range.

Accordingly, the finding by the inventors that a stable formulation of pimobendan can be prepared using propylene glycol without HPβCD has the advantage of providing formulations that are orally bioavailable and that may also be suitable for parenteral administration. This may assist administration of a pimobendan formulation to subjects and may also assist in the long term maintenance of treatment of a cardiac disease, for example, CHF or CVHD.

The liquid formulation may consist of, or comprise, a solution or an emulsion. A solution comprises one or more components dissolved in a liquid carrier. An emulsion comprises a liquid suspended in another liquid, typically with the aid of an emulsifier. A microemulsion is a thermodynamically stable solution that is clear upon visual inspection. For some microemulsions, one or more components may be suspended in a liquid carrier having a particle size that is too small to be observed by the eye.

The inodilator may be any compound that is capable of producing a positive inotropic effect and a vasodilatory effect when administered to a subject in need thereof. For example, the inodilator may be pimobendan, levosimendan, amrinone, enoximone, milrinone, olprinone, or vesnarinone. Typically, the inodilator may be pimobendan. As used herein, "inodilator" includes pimobendan, pharmaceutically and/or veterinary acceptable salts, derivatives, metabolites, stereoisomers or pro-drugs thereof.

The subject mentioned above may be a human or any animal that can benefit from treatment with an inodilator. The animal may be a mammal, typically a companion animal, such as a dog, horse or cat, but may also include other mammalian species. The term animal as used herein includes but is not limited to companion animals such as dogs, cats, guinea pigs, hamsters, horses, cattle, goats, sheep or the like. Typically, the subject is a dog, horse or cat, most typically a dog or a cat. However, animals in need of such treatment may also include zoo animals such as monkeys, elephants, giraffes and other ungulates, bears, mice and other small mammals.

In a preferred embodiment of the liquid formulation, the inodilator is pimobendan, pharmaceutically or veterinary acceptable salts, stereoisomers or metabolites thereof.

In the case of the pharmaceutically or veterinary acceptable salts these include, for example, inorganic salts such as chloride, sulfate, phosphate, diphosphate, bromide and/or nitrate salts. Furthermore, the formulations of the present invention may also contain organic salts such as malate, maleate, fumarate, tartrate, succinate, ethylsuccinate, citrate, acetate, lactate, methansulfonate, benzoate, ascorbate, paratoluensulfonate, palmoate, salicylate, stearate, estolate, gluceptate or lactobionate salts, for example. At the same time, corresponding salts may contain pharmaceutically acceptable cations such as sodium, potassium, calcium, aluminium, ammonium, for example.

The inodilator may be present in amounts of about 0.01 wt % to about 50 wt %, about 0.01 wt % to about 45 wt %, about 0.01 wt % to about 40 wt %, about 0.01 wt % to about 35 wt %, about 0.01 wt % to about 30 wt %, about 0.01 wt % to about 25 wt %, about 0.05 wt % to about 50 wt %, about 0.05 wt % to about 35 wt %, about 0.05 wt % to about 25 wt %, about 0.1 wt % to about 50 wt %, about 0.1 wt % to about 35 wt %, about 0.1 to about 25 wt %, about 1 wt % to about 50 wt %, about 1 wt % to about 35 wt %, about 1 wt % to about 25 wt %, about 0.01 wt % to about 20 wt %, 0.1 wt % to about 50 wt %, about 1 wt % to about 20 wt %, about 5 wt % to about 20 wt %, about 5 wt % to about 50 wt %, about 3 wt % to about 25 wt %, about 3 wt % to about 50 wt % or about 0.1 wt % to about 5 wt % of the total formulation.

In some embodiments, the inodilator is present in an amount of less than or equal to 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, 0.5, 0.3, 0.1, 0.05 or 0.01 wt % of the total formulation.

The formulation also comprises propylene glycol. Propylene glycol has a molecular formula of $C_3H_6(OH)_2$.

The inventors have surprisingly found that a liquid formulation comprising an inodilator and propylene glycol has comparable and, in some cases, superior bioavailability to that of the commercially available solid formulations of pimobendan in dogs. Notably, as shown in the bioavailability studies described herein, unlike the solid commercially available pimobendan formulation, the liquid formulation of the present invention does not require citric acid in order to exhibit effective oral bioavailability. Neither does the liquid formulation in the bioavailability studies described herein comprise a cyclodextrin, such as hydroxypropyl-beta-cyclodextrin.

Figure 3:
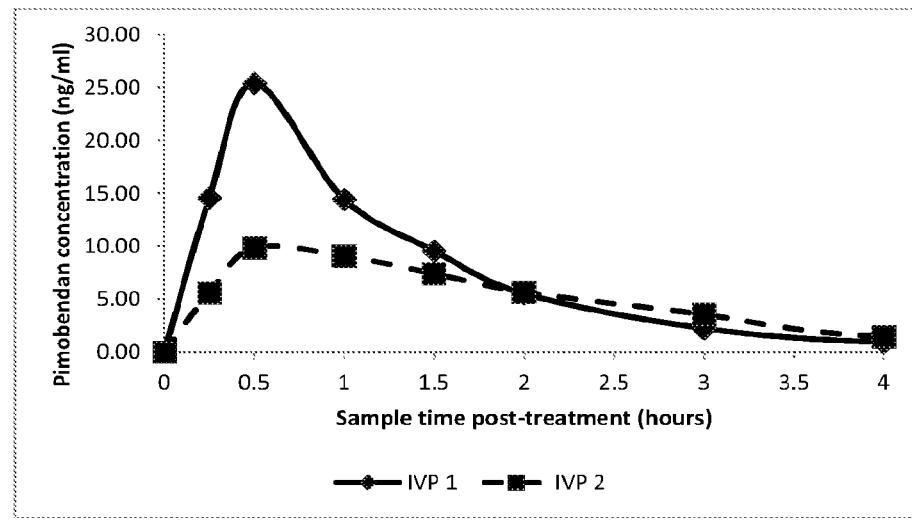
FIG. 3 is a graph which shows a comparison between plasma pimobendan concentrations in dogs after oral administration of a liquid formulation comprising pimobendan and propylene glycol, and a liquid formulation comprising pimobendan without propylene glycol.

The inventors have also found that a liquid formulation comprising pimobendan and propylene glycol more effectively provides bioavailable pimobendan after oral administration in dog than a liquid formulation comprising pimobendan in the absence of propylene glycol, see for example, Example 3 and FIG. 3.

The propylene glycol may be present in an amount of about 0.05 wt % to about 99.99 wt %, about 0.05 wt % to about 99.9 wt %, about 0.05 to about 99 wt %, about 0.05 wt % to about 97 wt %, about 0.05 wt % to about 55 wt %, about 0.05 wt % to about 50 wt %, about 0.05 wt % to about 65 wt %, about 5 wt % to about 99.99 wt %, about 10 wt % to about 99.99 wt %, about 20 wt % to about 99.99 wt %, about 5 wt % to about 60 wt %, about 5 wt % to about 50 wt %, about 10 wt % to about 50 wt %, or at least 20 wt % of the total formulation. For example, the propylene glycol may be present in an amount of at least 65, 60, 65, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, 0.75, 0.5, 0.2, 0.1 or 0.05 wt % of the total formulation. Any amount of propylene glycol mentioned herein can be used with any amount of inodilator, such as pimobendan, mentioned herein, provided that sufficient propylene glycol is used to solubilise the selected amount of the inodilator.

The general therapeutic effective target dose, in particular for the treatment of acute CHF, for example with pimobendan, but also for any other therapeutic use as described herein is about 0.05 to 1.0 mg pimobendan per kg body weight of the animal per day, typically about 0.1 to 0.5 mg pimobendan per kg body weight of the animal per day, even more typically about 0.5 mg pimobendan per kg body weight of the animal per day. The daily dose is typically divided and given as two equal doses and in severe cases three doses at approximately equally spaced time intervals. The target concentration of pimobendan in the drug product should suitably be set to 5.0 mg/ml allowing the administration of safe and even volumes. For example, a dog with a weight of 10 kg would receive exactly a dose of 0.5 ml containing 2.5 mg of pimobendan. The person skilled in the art would readily be able to adjust the amount of a liquid formulation depending on the weight and breed of the animal and other considerations, e.g. pre-existing conditions, diet of the animal, specific disease state and symptomatology, etc. Further, the person skilled in the art would readily be able to determine the required dose for other inodilators depending on the animal's disease state and severity in line with dosage recommendations and practises.

The ACVIM consensus recommendations for the chronic treatment of class III CVHD in dogs includes the combined treatment with pimobendan and an ACE-I, e.g. enalapril, or other suitable ACE-I, such as benazepril.

The inventors have found that a formulation comprising an ACE-I and propylene glycol provided orally bioavailable amounts of ACE-I in an animal, in particular in a dog, after administration.

Accordingly, one aspect provides a liquid formulation comprising an effective amount of an angiotensin converting enzyme inhibitor and propylene glycol.

The renin-angiotensin-aldosterone system (RAAS) is complex and when activated results in the elevation of blood pressure. Angiotensin II is a potent blood pressure regulator involved in RAAS that causes vasoconstriction. Thus lowering angiotensin II levels assists in reducing blood pressure by deactivating this aspect of the RAAS. The angiotensin converting enzyme (ACE) catalyses the conversion of angiotensin I into angiotensin II. Therefore, inhibition of ACE has been shown to be an effective antihypertensive agent to lower blood pressure in humans and animals alike. Further, as RAAS activation is one of the main causes for hypertension in animals, such as dogs and cats, an ACE-I is recommended as an initial therapy when an animal presents with hypertension.

Further, reduction of blood pressure is often useful in the treatment of cardiac conditions, such as CHF and CVHD.

Enalapril is an orally active prodrug of enalaprilat an inhibitor of ACE. Enalapril and enalaprilat have the following respective structures:

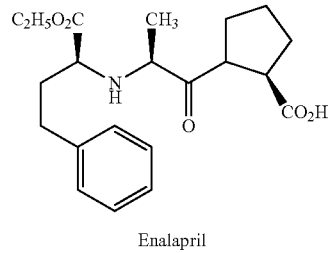

Enalapril

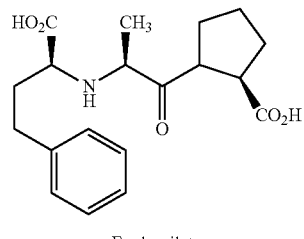

Enalaprilat

Benazepril is an orally active prodrug of benazeprilat another inhibitor of ACE. Benazepril and benazeprilat have the following respective structures:

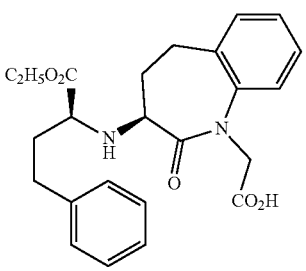

Benazepril

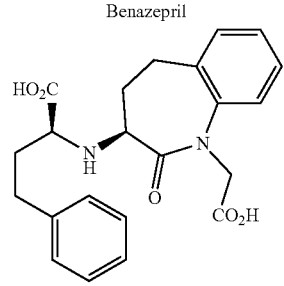

Benazeprilat

It will be appreciated that as used herein, a reference to an angiotensin converting enzyme inhibitor (ACE-I) is a reference to either the prodrug of an ACE-I or the active form of the ACE-I, i.e. it includes enalapril and enalaprilat, benazepril and benazeprilat, pharmaceutically and veterinary acceptable salts thereof, or a combination thereof. Other suitable ACE-I include alacepril, cilazapril, delapril, fosinopril, imidapril, moexipril, spirapril, temocapril, trandolapril, zofenopril, captopril, ramipril, quinapril, perindopril, lisinopril, and pharmaceutically and veterinary acceptable salts thereof, and prodrugs or corresponding active forms thereof, or a combination thereof.

The angiotensin converting enzyme may be present in amounts of about 0.01 wt % to about 50 wt %, about 0.01 wt % to about 45 wt %, about 0.01 wt % to about 40 wt %, about 0.01 wt % to about 35 wt %, about 0.01 wt % to about 30 wt %, about 0.01 wt % to about 25 wt %, about 0.05 wt % to about 50 wt %, about 0.05 wt % to about 35 wt %, about 0.05 wt % to about 25 wt %, about 0.1 wt % to about 50 wt %, about 0.1 wt % to about 35 wt %, about 0.1 wt % to about 25 wt %, about 1 wt % to about 50 wt %, about 1 wt % to about 35 wt %, about 1 wt % to about 25 wt %, about 0.01 wt % to about 20 wt %, 0.1 wt % to about 50 wt %, about 1 wt % to about 20 wt %, about 5 wt % to about 20 wt %, about 5 wt % to about 50 wt %, about 3 wt % to about 25 wt %, about 3 wt % to about 50 wt % or about 0.1 wt % to about 5 wt % of the total formulation.

In some embodiments, the angiotensin converting enzyme inhibitor is present in an amount of less than or equal to 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, 0.5, 0.3, 0.1, 0.05 or 0.01 wt % of the total formulation.

Propylene glycol may be present in a similar amount to that described above. Any amount of propylene glycol as described above may be used with any amount of ACE-I described above, provided that sufficient propylene glycol is used to solubilise the selected amount of ACE-I.

The general therapeutic effective target dose of an ACE-I, in particular for the chronic treatment of class III CVHD, but also for any other therapeutic use as described herein, is about 0.05 to 1.0 mg ACE-I per kg body weight of the animal per day, typically about 0.1 to 0.5 mg ACE-I per kg body weight of the animal per day, even more typically about 0.5 mg ACE-I per kg body weight of the animal per day. The daily dose is typically given as a single dose following water intake, however, in severe cases may be administered as two or three doses at approximately equally spaced time intervals in the course of a single day. The target concentration of ACE-I in the drug product should suitably be set to 5.0 to 10 mg/ml allowing the administration of safe and even volumes according to the selected ACE-I. For example, a dog with a weight of 10 kg would receive exactly a dose of 0.5 ml containing 2.5 mg or 5.0 mg of ACE-I. The person skilled in the art would readily be able to adjust the amount of a liquid formulation depending on the weight and breed of the animal and other considerations, e.g. pre-existing conditions, diet of the animal, specific disease state and symptomatology, etc. Further, the person skilled in the art would readily be able to determine the required dose to administer an effective amount of the specific ACE-I to be administered depending on the animal's disease state and severity in line with dosage recommendations and practises.

For example, the recommended dosage for enalapril for the chronic treatment of class III CVHD in dogs is about 0.5 mg/kg, PO q12h. The recommended dosage range for enalapril is 0.25 to 0.5 mg/kg, PO q12h or q24h. Similarly, the recommended dosage range for benazepril is 0.25 to 0.5 mg/kg, PO q12h or q24h.

It will be appreciated that similar to the inodilator liquid formulation described herein, administration of an ACE-I to a non-human animal, such as a dog or cat, via delivery of a liquid formulation is often easier than other forms of administration, for example, via a tablet. Further, there were no commercially available non-aqueous orally available ready-to-use liquid formulations of an ACE-I prior to the present invention. For the maintenance of chronic conditions in animals, such as dogs or cats, ready-to-use orally available liquid formulations are desirable.

As described herein, the inventors have found that a formulation comprising an inodilator, an ACE-I and propylene glycol provides plasma levels of active inodilator and ACE-I within the published therapeutic range.

Accordingly, one aspect provides a liquid formulation comprising propylene glycol and an effective amount of a combination of an inodilator and an angiotensin converting enzyme inhibitor.

Provision of a ready-to-use liquid formulation comprising a combination of an inodilator and an angiotensin converting enzyme inhibitor is advantageous for the reasons described above in relation to ease of dosing an active agent to an animal of a liquid formulation relative to other formulation types. Further, as inodilators and angiotensin converting enzyme inhibitors are often administered as a combination in the treatment of a cardiac disease, this formulation may assist in compliance with and maintenance of treatment.

The combination formulation comprises propylene glycol, an inodilator and an angiotensin converting enzyme inhibitor in amounts that are similar to those described above. The person skilled in the art will readily be able to determine the amounts of the inodilator and angiotensin converting enzyme inhibitor for inclusion in the combination formulation based on the recommended dosage for the particular agent selected. Further, the amount of the combination formulation to be administered will be readily appreciated based on the concentrations of each active and may be modulated depending on the factors described above, such as animal weight, disease state and severity, etc.

The formulations described herein may additionally comprise one or more pharmaceutically or veterinary acceptable excipient(s). The excipient may be any pharmaceutically or veterinary acceptable excipients for a liquid dosage form. The excipients which may be present in the formulation include a surfactant, a thickener, a flavour enhancer, a preservative, a solvent or a combination thereof.

For example, the formulation may comprise a surfactant. Surfactants are compounds that contain both a hydrophilic and a hydrophobic region within the same molecule, enabling them to reduce the interfacial tension between aqueous and non-aqueous phases so that mixing can occur. The surfactant may be an anionic surfactant, a cationic surfactant, an ampholytic surfactant or a non-ionic surfactant, or a combination of such surfactants may be used. Anionic surfactants include aluminium monostearate, calcium stearoyl-lactylate, sodium cetostearyl sulfate, sodium cocoyl isetionate, sodium cocoyl sarcosinate, sodium laurilsulfate, sodium lauroyl isetionate or sodium cocoyl isetionate, sodium lauroyl sarcosinate, sodium oleate, sodium stearate, sodium stearoyl-lactylate and sulfated castor oil. Cationic surfactants include tonzonium bromide. Ampholytic surfactants include aminocarboxylic acids, aminopropionic acid derivatives, imidazoline derivatives, and dodicin.

Non-ionic surfactants include acetoglycerides, diethylene glycol esters, diethylene glycol ethers, ethylene glycol esters, glyceryl behenate, glyceryl mono- and di-esters, glyceryl monocaprylocaprate, glyceryl monolinoleate, glyceryl mono-oleate, glyceryl stearates, macrogol cetostearyl ethers, macrogol/glycerol esters, macrogol 6 glyceryl caprylocaprate, macrogol 20 glyceryl monostearate, macrogol 15 hydroxystearate, macrogol laurates, macrogol lauril ethers, macrogol monomethyl ethers, macrogol oleates, macrogol oleyl ethers, macrogol 40 sorbitol heptaoleate, macrogol stearates, macrogolglycerol cocoates, nonoxinols, octoxinols, oleyl oleate, palmitic acid, poloxamers, polyoxyl castor oils, polyoxyl hydrogenated castor oils, polysorbates (e.g. polysorbate 80, polysorbate 60, polysorbate 40, polysorbate 20, etc.), polyvinyl alcohol, propylene glycol caprylates, propylene glycol diacetate, propylene glycol laurates, propylene glycol monopalmitostearate, quillaia, sorbitan esters, sucrose esters, triglycerol diisostearate, and tyloxapol.

The surfactant may be present in amounts of about 1 wt % to about 99 wt %, about 1 wt % to about 90 wt %, about 1 wt % to about 80 wt %, about 1 wt % to about 60 wt %, about 1 wt % to about 40 wt %, about 1 wt % to about 30 wt %, about 1 wt % to about 25 wt %, about 5 wt % to about 99 wt %, about 5 wt % to about 90 wt %, about 5 wt % to about 80 wt %, about 5 wt % to about 60 wt %, about 5 wt % to about 40 wt %, about 5 wt % to about 30 wt %, about 5 wt % to about 25 wt %, about 20 wt % to about 99 wt %, about 20 wt % to about 90 wt %, about 20 wt % to about 80 wt %, about 20 wt % to about 60 wt % or about 20 wt % to about 40 wt % of the total formulation.

For example, the formulation may comprise a viscosity modifier. The viscosity modifier may be any pharmaceutically or veterinary acceptable substance that modifies the viscosity of the liquid formulation to a suitable consistency for use. Thus, the viscosity modifier may be a thickener or a thinner. The viscosity modifier may be, for example, acacia, agar, alginic acid, aluminium magnesium silicate, aluminium monostearate, bentonite, carbomers, carmellose, carrageenan, cellulose, ceratonia, cetostearyl alcohol, cetyl alcohol, ethylcellulose, gellan gum, guaraprolose, hyetellose, hymetellose, hyprolose, hypromellose, methylcellulose, polyethylene oxide, polyvinyl acetate, polyvinyl alcohol, povidone, silicas, stearyl alcohol and tragacanth, or a combination thereof. Typically, the viscosity modifier may be a polyethylene glycol, such as PEG300, polypropylene glycol, microcrystalline cellulose, polyvinyl pyrrolidine or hydroxypropyl cellulose, or a combination thereof.

The viscosity modifier may be present in amounts of about 0.05 wt % to about 50 wt %, about 0.05 wt % to about 30 wt %, about 0.05 wt % to about 10 wt %, about 0.1 wt % to about 50 wt %, about 0.1 wt % to about 30 wt %, about 0.1 wt % to about 10 wt %, about 1 wt % to about 50 wt %, about 1 wt % to about 30 wt %, or about 1 wt % to about 10 wt % of the total formulation.

The formulation of the present invention may additionally comprise a flavour enhancer. The flavour enhancer may be any substance, or mixture, that enhances the flavour of the formulation for the subject in need thereof. The flavour enhancer may be a sweetener. Thus, the flavour enhancer may comprise a sugar substitute or another flavour, such as chicken or beef flavouring. For example, the flavour enhancer may be acesulfame potassium, alitame, aspartame, aspartame acesulfame, benzaldehyde, caramel, cyclamic acid, dibutyl sebacate, erythritol, ethyl acetate, ethyl cinnamate, ethyl maltol, ethyl vanillin, maltol, monosodium glutamate, neohesperidin dihydrochalcone, neotame, raspberry, red cherry, saccharin, saffron, stevioside, sucrose octa-acetate, thaumatin, theobroma, tributyl acetylcitrate, vanilla, vanillin, xylitol, dextrose, sucrose or glucose, or a combination thereof. Typically, the flavour enhancer may be selected from the group consisting of acesulfame potassium and stevioside, or a combination thereof.

The flavour enhancer may be present in amounts of about 0.1 wt % to about 40 wt %, 0.1 to about 20 wt %, about 5 wt % to about 40 wt % or about 5 wt % to about 20 wt % of the total formulation.

The formulation of the present invention may also comprise a preservative. The preservative may be an antioxidant, anti-microbial, free-radical scavenger or any other agent that extends the shelf-life of the formulation. For example, the preservative may be benzoic acid, sodium benzoate, sodium propionate, sorbic acid, benzyl alcohol, bronopol, chlorbutol, phenoxyethanol, o-phenoxyethanol, chlorhexidine salts, hydroxybenzoate derivatives, phenylmercuric salts, thiomersal, chlorocresol, cresol, phenol, benzalkonium chloride, cetrimide, alpha-tocopherol, ascorbic acid, sodium ascorbate, butylated hydroxyanisole, butylated hydroxytoluene or sodium metabisulfite, or a combination thereof. Typically, the preservative may be benzyl alcohol, phenoxyethanol, o-phenylethanol or phenol, or a combination thereof. More typically, the preservative may be benzyl alcohol.

The preservative may be present in the formulation in amounts of about 0.001 wt % to 10 wt %, about 0.001 to about 1 wt %, about 0.01 to about 10 wt % or about 0.01 wt % to about 1 wt % of the total formulation.

The formulation of the present invention may also comprise a solvent in addition to propylene glycol. For example, the solvent may be glycerol, ethanol, propanol, butanol, amyl acetate, amylene hydrate, butylenes glycol, glycerol formol, hexylene glycol, polyethylene glycol e.g. PEG300, glycofurol, pyrrolidone, propylene glycol diacetate, or a vegetable oil, such as canola oil, olive oil, castor oil, peanut oil, etc., or a combination thereof. Typically, the solvent may be glycerol or PEG300.

The solvent may be present in the formulation in amounts of about 1 wt % to about 99.94 wt %, about 1 wt % to about 90 wt %, about 1 wt % to about 75 wt %, about 1 wt % to about 70 wt %, about 1 wt % to about 65 wt %, about 1 wt % to about 60 wt %, about 1% to about 50 wt % about 7 wt % to about 99.94 wt %, about 7 wt % to about 90 wt %, about 7 wt % to about 75 wt %, about 7 wt % to about 70 wt %, about 7 wt % to about 65 wt %, about 7 wt % to about 60 wt %, about 7% to about 50 wt %, about 15 wt % to about 99.94 wt %, about 15 wt % to about 90 wt %, about 15 wt % to about 75 wt %, about 15 wt % to about 70 wt %, about 15 wt % to about 65 wt %, about 15 wt % to about 60 wt % or about 15% to about 50 wt % of the total formulation.

It will be appreciated by the person skilled in the art that an excipient, e.g. a flavour enhancer such as orange, lemon or lime flavour, may contain small amounts of citric acid. When such an excipient is incorporated into the liquid formulation described herein the amount of citric acid is less than an amount required to provide a bioavailable amount of an inodilator, such as, pimobendan, to the animal after oral administration. These formulations will contain citric acid in a ratio of less than 1:10 pimobendan to citric acid.

Accordingly, another aspect provides an orally available liquid formulation comprising an inodilator, such as pimobendan, and excluding an acidic solubility enhancer, such as citric acid. In an embodiment, a formulation according to this aspect comprises citric acid in an amount of less than about 5, 4, 3, 2, 1, 0.5, 0.05, or 0.01 wt % of the total formulation, typically none.

In addition to the excipients, the formulation of the present invention may also comprise one or more further active agent(s). As used herein, an "active agent" relates to a compound that following administration provides a therapeutic effect in a subject, put another way the active agent is a pharmaceutical or veterinary substance. Further active agents that can be administered with an inodilator, such as pimobendan, and/or an ACE-inhibitor such as, for example, enalapril or benazepril, for the treatment of a cardiac disease, such as CFH, CVHD or other cardiac conditions discussed above, are known in the art, and include a diuretic, such as, for example, furosemide, spironolactone, chlorthalidone or hydrochlorothiazide, or a combination thereof. Further active agents that can be administered with an ACE-inhibitor for the treatment of hypertension include calcium channel blockers, such as, for example, amlodipine.

The further active agent may be present in amounts of about 0.01 wt % to about 50 wt %, about 0.01 wt % to about 45 wt %, about 0.01 wt % to about 40 wt %, about 0.01 wt % to about 35 wt %, about 0.01 wt % to about 30 wt %, about 0.01 wt % to about 25 wt %, about 0.05 wt % to about 50 wt %, about 0.05 wt % to about 35 wt %, about 0.05 wt % to about 25 wt %, about 0.1 wt % to about 50 wt %, about 0.1 wt % to about 35 wt %, about 0.1 to about 25 wt %, about 1 wt % to about 50 wt %, about 1 wt % to about 35 wt %, about 1 wt % to about 25 wt %, about 0.01 wt % to about 20 wt %, 0.1 wt % to about 50 wt %, about 1 wt % to about 20 wt %, about 5 wt % to about 20 wt %, about 5 wt % to about 50 wt %, about 3 wt % to about 25 wt %, about 3 wt % to about 50 wt % or about 0.1 wt % to about 5 wt % of the total formulation.

In some embodiments, the further active agent is present in an amount of less than or equal to 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, 0.5, 0.3, 0.1, 0.05 or 0.01 wt % of the total formulation.

It will be appreciated that any of the above amounts of further active agent can be used with any amount of inodilator and/or ACE-I defined above. The relative amounts of the inodilator, ACE-I and further active agent may be selected according to the relative recommended dosage of each.

In an embodiment, the liquid formulation may comprise a diuretic, such as furosemide, spironolactone, chlorthalidone or hydrochlorothiazide or a veterinary or pharmaceutically acceptable salt thereof.

Furosemide (sometimes referred to as frusemide) is a diuretic of the following formula:

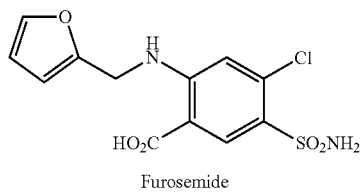 [SMILES: NS(=O)(=O)c1cc(C(=O)O)c(NCc2ccco2)cc1Cl]

Furosemide

Furosemide is a loop diuretic and its use in the treatment of hypertension and edema has been described. Furosemide is recommended for the acute or chronic treatment of class III CVHD in dogs. The consensus recommended dosage of furosemide for acute class III CVHD should be in line with the severity of clinical signs and the response to an initial dose, for example, a dosage of about 1 to about 4 mg/kg. For chronic treatment higher dosages are recommended, for example greater than or equal to 6 mg/kg q12h, or as much as required to maintain comfort in the animal patient.

It will be appreciated that a reference to a "diuretic" includes a reference to a pharmaceutically or veterinary acceptable salt thereof, or a prodrug thereof. Suitable diuretics include furosemide, hydrochlorothiazide, bumetanide, ethacrynic acid, torasemide, chlorothiazide, chlorthalidone, spironolactone, triamterene, amiloride, a pharmaceutically or veterinary acceptable salt thereof, or a combination thereof.

When a liquid formulation of the invention contains furosemide, or another diuretic, the person skilled in the art would readily be able to adjust the dosage of the liquid formulation depending on the weight and breed of the animal and other considerations, e.g. pre-existing conditions, diet of the animal, specific disease state and symptomatology, etc. Further, the person skilled in the art would readily be able to determine the required dose for the specific diuretic, e.g. furosemide, to be administered depending on the animal's disease state and severity in line with dosage recommendations and practises.

Another aspect provides a liquid formulation comprising an active agent and propylene glycol, wherein the active agent is selected from the group consisting of an inodilator, an ACE-I, a diuretic and a combination thereof.

In an embodiment, the liquid formulation according to this aspect comprises an active agent selected from the group consisting of pimobendan, enalapril, benazepril, furosemide, hydrochlorothiazide and veterinary and pharmaceutically acceptable salts thereof.

In some embodiments, the formulation of the present invention is suitable for oral administration. By oral administration it is meant that the active agent is bioavailable after administering the formulation to a subject in need thereof by mouth. For formulations of the invention comprising an inodilator, following oral administration of an amount of the formulation an effective amount of the inodilator is bioavailable and present at therapeutic concentrations in the plasma of the animal patient. For formulations of the invention comprising an ACE-I, following oral administration an effective amount of the active form of the ACE-I is bioavailable and present at therapeutic concentrations in the blood plasma of the animal patient. Absorption through the oral or buccal mucosa, gastro-intestinal tract, or any other route available for drug absorption when administered by mouth is included.

Preferably, the liquid formulations of the present invention form a clear solution when added to water over a full range of pH, e.g. about 1 to about 9. For example, the liquid formulation forms a clear aqueous solution when added to water at pH of about 1 to about 2, about 6 to about 8 or about 8 to about 9. These solutions mimic the pH conditions of various biological environments, for example, pH 8 to 9 is intended to mimic the pH of the mouth, neutral pH of about pH 6 to 8 mimics the small intestine and pH of about 1 to 2 mimics the stomach. When a liquid formulation forms a clear solution with water adjusted to each of these pH ranges, it is an indication that the pimobendan will remain in solution and that it may be bioavailable after oral administration to a subject in need thereof.

In some embodiments, the formulation may be in the form of a sterile injectable aqueous or oleagenous solution, emulsion or suspension. This suspension may be formulated according to the known art using those suitable dispersing or wetting agents and suspending agents. The sterile injectable preparation may also be a sterile injectable solution or suspension in a non-toxic parenterally-acceptable diluent or solvent, for example in admixture with N-methylpyrrolidone, with additional propylene glycol, or may be suitable without any further additive. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectable formulations. The injectable formulations may be administered by bolus injection, by intravenous (IV), intramuscular (IM) and/or by sub-cutaneous (SC) routes.

Thus in general the liquid formulation may be administered alone or in the form of a solution, emulsion or suspension. Thus, the liquid formulation may be administered directly, or alternatively may be diluted with a suitable carrier or diluents. For example, the carrier or diluents may be water, glycerol, alkyl benzoate, beeswax, calcium sulfate, candelilla wax, cellulose, cetostearyl alcohol, cetyl alcohol, cetyl esters, cholesterol, coconut oil, cottonseed oil, creatinine, dextrates, dimethyl sulfoxide, emulsifying waxes, erythritol, ethyl oleate, glyceryl stearates, hard fat, hard paraffin, isopropyl myristate, isopropyl palmitate, macrogol monomethyl ethers, liquid paraffin, microcrystalline wax, myristyl alcohol, oleic acid, oleyl alcohol, palm oil, polydextrose, shea butter, silicones, soft paraffin, squalane, stearyl alcohol, theobroma, wool alcohols, wool fat and vegetable fatty oils, or a combination thereof.

Solutions and suspensions will generally be aqueous, for example prepared from water alone (for example sterile or pyrogen-free water) or water and a physiologically acceptable co-solvent (for example ethanol or polyethylene glycols such as PEG 400).

Such solutions or suspensions may additionally contain other excipients for example preservatives (such as benzalkonium chloride), solubilising agents/surfactants such as polysorbates (for example Tween 80, Span 80, benzalkonium chloride), buffering agents, isotonicity-adjusting agents (for example sodium chloride), absorption enhancers and viscosity enhancers. Suspensions may additionally contain suspending agents (for example microcrystalline cellulose and carboxymethyl cellulose sodium).

When desired, formulations adapted to give sustained release of the active compound may be employed.

The formulation of the present invention may also be administered rectally. In these embodiments, the formulation is applied to the rectum of the subject, and may be in the form of a solution or suspension, as described above.

The liquid formulation may be presented for use in the form of veterinary compositions, which may be prepared, for example, by methods that are conventional in the art. Examples of such veterinary compositions include those adapted for:

(a) oral administration, external application, for example drenches (e.g. aqueous or non-aqueous solutions or suspensions); liquid filled capsules or boluses; powders, tablets comprising granules or pellets comprising the liquid formulation described herein and may be, for example, used in admixture with feed stuffs; pastes for application within the buccal cavity or to the tongue;

(b) parenteral administration for example by subcutaneous, intramuscular or intravenous injection, e.g. as a sterile solution or suspension;

(c) topical applications; or (d) rectally or intravaginally.

In order to easily facilitate combination therapy, the formulations defined above may be provided as part of a kit comprising combinations of active agents.

Accordingly, one aspect provides a kit comprising a first formulation comprising an effective amount of an inodilator, and a second formulation comprising an effective amount of an angiotensin converting enzyme inhibitor, wherein the first and second formulations are held separately and at least one of the first and the second formulations comprises propylene glycol.

Another aspect provides a kit comprising a first formulation comprising an effective amount of an inodilator or an angiotensin converting enzyme inhibitor and a second formulation comprising a further active agent, wherein the first and second formulations are held separately and at least one of the first and the second formulations comprises propylene glycol.

The inodilator and/or angiotensin converting enzyme inhibitor of the kits defined above may be any suitable inodilator or angiotensin converting enzyme inhibitor described herein. In one embodiment, the inodilator is pimobendan or a pharmaceutically or veterinary acceptable salt thereof. In another embodiment, the angiotensin converting enzyme inhibitor is selected from the group consisting of enalapril, benazepril, pharmaceutically or veterinary acceptable salts thereof, or a combination thereof.

The first and second formulations may be held separately each in a container. The container may be suitable for both storing and dispensing the formulation. Containers suitable for storage include, for example, a blister pack, vial, ampoule or the like. When such a container is used the kit may additionally comprise a dispenser, such as a syringe or a receptacle with volumetric markings. Containers suitable for both storage and dispensing the liquid formulations include, for example, a syringe, a receptacle with volumetric markings, a sponge soaked in the liquid formulation, and the like.

In some embodiments, the kit is adapted to administer the first and second formulations separately, sequentially or simultaneously. Separate, sequential or simultaneous administration includes administrations via different routes, e.g. the first formulation may be administered orally and the second formulation may be administered parenterally. Further, separate and sequential administration includes administration by the same or different route the first and second formulations at different times, e.g. up to 6 hours apart, generally within about 2 hours of each other.

In some embodiments, both first and second formulations comprise propylene glycol. In these embodiments, the first and second formulations may be combined prior to their administration.

In an embodiment, the kit comprises a further formulation comprising an effective amount of a further active agent. Typically, this formulation is a liquid formulation.

The further active agent may be a diuretic, such as any of the suitable diuretics described above, including furosemide, chlorthialidone, hydrochlorothiazide and pharmaceutically or veterinary acceptable salts thereof, or a combination thereof, or may include a calcium channel blocker as described above. Alternatively, if the kit already comprises a diuretic the further active agent may be any one of an inodilator, an angiotensin converting enzyme inhibitor or a calcium channel blocker such that the kit comprises the combination of an inodilator, an angiotensin converting enzyme inhibitor and a diuretic.

In another embodiment, the kit comprises instructions for use.

Process

The liquid formulation may be prepared by mixing, with or without the addition of heat, an effective amount of an inodilator and/or an angiotensin converting enzyme inhibitor with propylene glycol and then, progressively adding any of the desired excipients or further active agents mentioned above if desired.

Accordingly, another aspect of the invention provides a process for the preparation of a liquid formulation comprising an effective amount of an inodilator, an angiotensin converting enzyme inhibitor or a combination of an inodilator and an angiotensin converting enzyme inhibitor and propylene glycol, comprising mixing an effective amount of the inodilator or angiotensin converting enzyme inhibitor with propylene glycol.

In an embodiment, the process further comprises the sequential addition of one or more of the following excipients: a surfactant, a viscosity modifier, a flavour enhancer, a preservative, and a solvent, or a combination thereof.

For example, the following protocol can be used to prepare a liquid formulation containing:

| | |
|---|---|
| Inodilator | 0.25 g |
| Propylene glycol | 23 ml |
| Preservative | 0.05 ml |
| Viscosity modifier | 10 ml |
| Flavour enhancer | 0.2 g |
| Surfactant | 0.3 ml |
| Solvent | to 50 ml |

Step 1 Dissolve inodilator in propylene glycol (15 ml) while heating to about 65° C.
Step 2 Add solvent (5 ml) with stirring.
Step 3 Add preservative with stirring.
Step 4 Add viscosity modifier with stirring.
Step 5 In a separate vessel, dissolve flavour enhancer in propylene glycol (5 ml) with stirring.
Step 6 Transfer solution prepared in Step 5 to bulk solution prepared in Step 4 with stirring.
Step 7 In a separate vessel disperse and dissolve surfactant in propylene glycol (3 ml) and solvent (3 ml). Heat solution to about 65° C. prior to addition to the bulk.
Step 8 Combine solution prepared in Step 6 with the bulk. Mix until clear. Allow to cool.
Step 9 Add solvent to final batch volume.

In embodiments of liquid formulations comprising active agents other than an inodilator, including for liquid formulations comprising a combination of an inodilator and another active agent, the method described above comprises an additional step of dissolving the active agent in propylene glycol with stirring with or without heat as required. The addition of the additional active agent will often be conducted concurrently with or immediately following step 1, above.

For embodiments comprising an angiotensin converting enzyme inhibitor (ACE-I) and propylene glycol, the ACE-I is substituted for the inodilator in a method similar to that described above.

Methods of Use

The formulation may be used in the treatment of diseases, wherein cardiotonic, hypotensive, anti-inflammatory and anti-thrombotic substances have a therapeutic benefit. Such diseases include cardiac disease and hypertension.

Cardiac disease includes primary and secondary heart disease. Primary heart disease includes, for example, congestive heart failure (CHF), acute CHF, chronic CHF, decompensated endocardiosis (DCE), dilated cardiomyopathy (DCM), asymptomatic (occult) CHF, asymptomatic DCM, and chronic valvular heart disease, or a combination thereof.

Secondary heart disease includes, for example, cardiovascular dysfunction and impaired renal perfusion during anaesthesia, shock, gastric dilation, volvulus, myocardial ischaemia, and renal ischaemia, or a combination thereof.

Accordingly, one embodiment provides a method of treating a primary or secondary heart disease, comprising administering the formulation defined above to a subject in need thereof.

Hypertension is commonly associated with activation of the Renin-Angiotensin-Aldosterone System (RAAS) as described above. Disorders associated with hypertension include hyperadrenocorticism, hyperthyroidism, phaeochromocytoma, primary hyperaldosteronism, diabetes mellitus, and renal disease, or a combination thereof.

Accordingly, one embodiment provides a method of treating a disease or disorder associated with activation of the renin-angiotensin-aldosterone system (RAAS).

There is also provided use of propylene glycol and an effective amount of an inodilator, an angiotensin converting enzyme inhibitor or a combination of an inodilator and an angiotensin converting enzyme inhibitor, in the manufacture of a liquid formulation for the treatment of a cardiac disease and/or hypertension.

There is also provided a liquid formulation comprising propylene glycol and an effective amount of an inodilator, an angiotensin converting enzyme inhibitor or a combination of an inodilator and an angiotensin converting enzyme inhibitor for use in the treatment of a cardiac disease and/or hypertension.

There is also provided use of a liquid formulation comprising propylene glycol and an effective amount of an inodilator, an angiotensin converting enzyme inhibitor or a combination of an inodilator and an angiotensin converting enzyme inhibitor for treating a cardiac disease and/or hypertension.

In one embodiment, the primary heart disease is selected from the group consisting of congestive heart failure (CHF), acute CHF, chronic CHF, decompensated endocardiosis (DCE), dilated cardiomyopathy (DCM), asymptomatic (occult) CHF, asymptomatic DCM, and chronic valvular heart disease, or a combination thereof.

In one embodiment, the secondary heart disease is selected from the group consisting of cardiovascular dysfunction and impaired renal perfusion during anaesthesia, shock, gastric dilation, volvulus, myocardial ischaemia, and renal ischaemia, or a combination thereof.

In some embodiments, the subject is a companion animal, such as a dog or a cat.

In some embodiments, the administration is oral administration. Whereas, in others, the administration is parenteral administration.

As will be apparent to a person skilled in the art, an effective amount of the active agent, such as an inodilator, ACE-I or diuretic, will depend on a variety of factors, including the activity of the specific active agent selected, the weight of the subject in need of treatment, and type and severity of the condition to be treated. The skilled person will readily be able to determine an effective amount of the active agent, such as the inodilator, ACE-I or diuretic, to be administered to the subject in need of treatment, and based on this effective amount, determine the amount of the formulation of the present invention to be administered.

As described supra, the general therapeutically effective amount of pimobendan is about 0.2 to 1.0 mg pimobendan per kg body weight of the animal and application, typically about 0.3 to 0.6 mg pimobendan per kg body weight of the animal and application, even more typically about 0.5 mg pimobendan per kg body weight of the animal. Typically, two doses are administered per day, each dose representing one half of the effective amounts mentioned above. In some cases, a third dose may be administered. Liquid formulations of pimobendan with sustained absorption may be suitable for once daily administration.

For example, the therapeutically effective amount for the treatment of CHF is about 0.2 to about 1.0 mg pimobendan per kg body weight of the animal per day, preferably about 0.3 to about 0.6 mg pimobendan per kg body weight of the animal, even more preferably about 0.5 mg pimobendan per kg body weight of the animal. Typically, two doses are administered per day, one dose in the morning and the other approximately 12 hours later. Such a treatment is also advantageous in the case of maintenance of cardiovascular function and/or renal perfusion during anaesthesia, shock, gastric dilation or volvulus, for example caused by surgery, especially gastrointestinal surgery as well as trauma.

The general therapeutically effective amounts of the ACE-I enalapril and benazepril are described supra. Also described supra is the general therapeutically effective amount of furosemide.

Generally, the term "treatment" means affecting a subject, tissue or cell to obtain a desired pharmacological and/or physiological effect and includes: (a) inhibiting the disease, i.e. arresting its development or further development; (b) relieving or ameliorating the effects of the disease, i.e. cause regression of the effects of the disease; (c) reducing the incidence of the disease or (d) preventing the disease from occurring in a subject, tissue or cell predisposed to the disease or at risk thereof, but has not yet been diagnosed with a protective pharmacological and/or physiological effect so that the disease does not develop or occur in the subject, tissue or cell.

Reference is made hereinafter in detail to specific embodiments of the invention. While the invention is described in conjunction with these specific embodiments, it will be understood that it is not intended to limit the invention to such specific embodiments. On the contrary, it is intended to cover alternatives, modifications, substitutions, variations and equivalents as may be included within the spirit and scope of the invention as defined by the appended claims.

EXAMPLES

Example 1

Solubility Studies of Pimobendan

Each formulation was prepared by dissolving the pimobendan in propylene glycol or other solvent as described in Tables 1 to 4 and then progressively adding the remaining constituents while the pimobendan and solvent were stirred with a magnetic stirrer. Once each test formulation was prepared, a one ml sample was taken by single use pipette or syringe and added to 100 ml water of pH 1-2, 7 or 9. Acid water was prepared by the addition of hydrochloric acid to distilled water, monitoring the pH with an electronic pH meter until the desired pH was obtained. Alkaline water was prepared by adding sodium hydroxide to distilled water, monitoring the pH change with a pH meter and ceasing addition of NaOH when the desired pH was reached.

After addition and thorough mixing of 1 ml each test formulation in 100 ml samples of the three waters of different pHs, the visual appearance of each mixture was noted and recorded and summarised in the Tables 1 to 4.

TABLE 1

Solubility of pimobendan

| CONSTITUENT | V5 + stevia + Chicken Flavour | V5 + stev + Beef Flavour | V5 | V6 | V7 |
|---|---|---|---|---|---|
| Pimobendan | 0.5 | 0.5 | 0.5 | 0.5 | 0.5 |
| Caprylic/capric TGs | | | 0 | 0 | 0 |
| Castor oil | | | | | |
| Polysorbate 80 | qs100 | qs100 | qs100 | qs100 | qs100 |
| Propylene glycol | 20 | 20 | 20 | 10 | 5 |
| Water | | | | | |
| DESCRIPTION | Yellow clear | Yellow clear | Yellow clear | | |
| DILUTION IN SIMULATED GASTRIC FLUID | Clear liquid No oil layer | Clear liquid No oil layer | Clear liquid No oil layer | Clear liquid No oil layer | Clear liquid No oil layer |

TABLE 1-continued

Solubility of pimobendan

| CONSTITUENT | V5 + stevia + Chicken Flavour | V5 + stev + Beef Flavour | V5 | V6 | V7 |
|---|---|---|---|---|---|
| DILUTION IN WATER at neutral ph - 7 and pH 9 | Clear liquid No oil layer | Clear liquid No oil layer | Clear liquid No oil layer | Clear liquid No oil layer | Clear liquid No oil layer |

TABLE 2

Comparative pimobendan solubilities

| CONSTITUENT | V1 | Castor oil + water |
|---|---|---|
| Pimobendan | 0.5 | 0.5 |
| Caprylic/capric TGs | 40 | |
| Castor oil | | 20 |
| Polysorbate 80 | qs100 | 0 |
| Propylene glycol | 20 | 0 |
| Water | | 100qs |
| DESCRIPTION | Cloudy translucent | Did not dissolve |
| DILUTION IN SIMULATED GASTRIC FLUID | White liquid, sheen of oil layer on top no droplets | |
| DILUTION IN WATER at neutral ph - 7 and pH 9 | White liquid, sheen of oil layer on top no droplets | |

TABLE 3

Solubility of pimobendan

| CONSTITUENT | N2 | IVPi |
|---|---|---|
| Pimobendan | 0.5 | 0.25 g |
| Caprylic/capric TGs | 0 | 0 |
| Polysorbate 80 | 100 qs | 0 |
| Propylene glycol | 20 | 23 |
| Ethanol 200 proof | Wet | 0 |
| Polyethylene glycol 300 | | 10 |
| Benzyl alcohol | | 0.05 |
| Stevioside | | 0.1 |
| Acesulfame potassium | | 0.1 |
| Polyvinyl pyrrolidone | | 0.3 |
| Glycerol | | qs 50 ml |
| Lot number | | 0405@54 |
| DESCRIPTION | Clear yellow | Clear yellow |
| DILUTION IN SIMULATED GASTRIC FLUID - description | Clear liquid No oil layer | Clear liquid No oil layer |
| DILUTION IN WATER at neutral ph - description | Clear liquid No oil layer | White liquid |

TABLE 4

Comparative pimobendan solubility

| CONSTITUENT | N1 | A_V1 | A_V2 |
|---|---|---|---|
| Pimobendan | 0.5 | 0.5 | 0.5 |
| Caprylic/capric TGs | 0 | 40 | 20 |
| Polysorbate 80 | qs 100 | qs 100 | qs 100 |
| Propylene glycol | Wet | 0 | 0 |
| Ethanol 200 proof | 0 | WET | WET |
| Polyethylene glycol 300 | | | |
| Benzyl alcohol | | | |
| Stevioside | | | |
| Acesulfame potassium | | | |
| Polyvinyl pyrrolidone | | | |
| Glycerol | | | |
| Lot number | 0405@21 | 0405@4 | 0405@7 |
| DESCRIPTION | Yellow transparent | Cloudy translucent | Clear few specks |
| DILUTION IN SIMULATED GASTRIC FLUID - description | Clear but lumpy gel were formed | White liquid, sheen of oil layer on top no droplets | Clear but lumpy gel were formed. |
| DILUTION IN WATER at neutral ph - description | Clear but lumpy gel were formed | White liquid, sheen of oil layer on top no droplets | Clear but lumpy gel were formed. |

Example 2

Bioavailability Study

Six adult dogs in good health were selected for inclusion. All dogs underwent a general physical examination (GPE), including weighing prior to the example's commencement. Dogs with a cardiovascular abnormality evident on GPE were not included.

The bioavailability of orally administered pimobendan is reported to be considerably reduced when administered with food or shortly thereafter. Therefore, feed was withheld for a minimum of 4 hours prior to treatment and for 1 hour post-treatment. Other than Day 0, dogs were fed a commercial dry dog food to maintenance level. Dogs had access to fresh water at all times.

The laboratory was blinded to the treatment allocation of each dog/group. The administering staff were not blinded to the treatment groups.

Two different formulations were assessed—the investigational veterinary product or IVP—Pimobendan 5 mg/mL liquid formulation (detailed below) and the reference veterinary product or RVP—Vetmedin® (1.25, 2.5 & 5 mg) capsules (Boehringer Ingelheim).

Treatments were administered to each dog once on Day 0. Blood samples were collected at predetermined intervals (Table 5) and analysed.

IVP Liquid Formulation:

| | |
|---|---|
| Pimobendan | 0.5 g |
| Propylene glycol | 23 ml |
| PEG 300 | 10 ml |
| PVP | 0.3 g |
| Glycerol | qs 50 ml |

Trial animals were treated as per the schedule outlined in Table 5. Individual doses were calculated according to the dog's bodyweight as recorded in the immediate pre-trial period.

TABLE 5

Schedule of Events

| Day of Trial | Event |
|---|---|
| \multicolumn{2}{c}{PHASE ONE} | |
| Pre-trial | Select dogs for inclusion |
| | General Physical Examination & weigh dogs |
| | Group allocation of all dogs into 2 groups - A and B |
| Pre-trial | Acclimatisation; dogs fed dry commercial feed once daily |
| Day 0 | Daily observation record |
| | Group A treated with the IVP and Group B treated with the RVP once only at time 0 |
| | Blood samples collected at pre-treatment, then at 0.25, 0.5, 1, 1.5, 2, 3 and 4 hours post-treatment and times of collection recorded |
| | Centrifuge, label, freeze and store samples in duplicate; one set transported to designated laboratory and one set retained |

The recommended dose for Vetmedin® in the dog is 0.2-0.6 mg/kg. The preferable daily dose is 0.5 mg/kg bodyweight. The dose should be divided into two administrations at approximately 12 hour intervals. Each dose should be given approximately one hour before feeding (Boehringer Ingelheim, Australian Pesticides and Veterinary Medicines Authority (APVMA) approved label).

In this example, the dogs were dosed once with half the recommended total daily dose—i.e. 0.25 mg pimobendan/kg bodyweight.

As the capsule presentation is the limiting factor for the RVP dose in this example, all doses were rounded to the nearest multiple of 1.25 mg pimobendan per dog corresponding to the smallest available capsule dosage. A combination of capsule sizes was used to achieve the most accurate dose of the pimobendan for each dog where appropriate.

The dose for the IVP was based on the equivalent dose in capsules for the dogs' bodyweight.

TABLE 6

Dose of pimobendan (mg of pimobendan)
Pimobendan Dosage: 0.25 mg/kg

| Bodyweight | Dose | RVP (Number of Capsules) capsule size | | | actual dose pimobendan | IVP (to match the RVP dose for this size dog) | actual dose pimobendan |
|---|---|---|---|---|---|---|---|
| (kg) | (mg) | 1.25 mg | 2.5 mg | 5 mg | RVP (mg/kg) | 5 mg/ml | IVP (mg) |
| 10 | 2.5 | | 1 | | 0.25 | 0.50 | 2.5 |
| 11 | 2.75 | | 1 | | 0.23 | 0.50 | 2.5 |
| 12 | 3 | | 1 | | 0.21 | 0.50 | 2.5 |
| 13 | 3.25 | 1 | 1 | | 0.29 | 0.75 | 3.75 |
| 14 | 3.5 | 1 | 1 | | 0.27 | 0.75 | 3.75 |
| 15 | 3.75 | 1 | 1 | | 0.25 | 0.75 | 3.75 |
| 16 | 4 | 1 | 1 | | 0.23 | 0.75 | 3.75 |
| 17 | 4.25 | 1 | 1 | | 0.22 | 0.75 | 5 |
| 18 | 4.5 | | | 1 | 0.28 | 1.00 | 5 |
| 19 | 4.75 | | | 1 | 0.26 | 1.00 | 5 |
| 20 | 5 | | | 1 | 0.25 | 1.00 | 5 |

The IVP and RVP were administered orally.

Oral administration of the IVP involved drawing up the required dose into a syringe. The syringe was introduced to the dog's mouth at the commissure of the lips and the dose deposited on the back of the tongue. The dog's mouth was held closed and the head tilted back slightly to ensure that the entire amount of administered product was swallowed.

The RVP capsules were deposited over the base of the tongue at the back of the oral cavity and the dogs' mouth held closed and the head tilted back slightly to ensure that the capsule is swallowed.

Each dog was closely observed after treatment to ensure that the IVP and RVP were not regurgitated or otherwise expelled.

Dogs were fasted overnight and the morning feed withheld until 1 hour post-dosing. Treatment was undertaken as close to 8 AM as possible.

After oral administration to 3 dogs in each group at a dose rate of 0.25 mg pimobendan/kg bodyweight the following plasma concentrations (ng/ml) of pimobendan were observed.

TABLE 7

Mean results of oral dosing of pimobendan (ng/mL)

| Treatment | Pre | Sampling time (hours) | | | | | | |
|---|---|---|---|---|---|---|---|---|
| | | 0.25 | 0.5 | 1 | 1.5 | 2 | 3 | 4 |
| IVP | <0.5 | 4.0 | 7.8 | 11.8 | 9.9 | 6.9 | 2.8 | 1.2 |
| RVP | <0.5 | 1.9 | 8.9 | 15.9 | 8.3 | 4.5 | 1.3 | 0.8 |

Plasma samples were analysed using a validated analytical method based on separation and quantitation using Ultra High Performance Liquid Chromatography and tandem mass spectrometry. Quantitative data is reported in ng/mL in tabular and graphical form. All but one dog exhibit typical absorption and elimination profiles, but the variation of absorption for both products is varied.

The data indicates that pimobendan is rapidly absorbed following administration of the IVP, and pimobendan remains in systemic circulation at concentrations higher than the lower limit of quantitation (LLOQ) for more than four hours. Based on the pharmacokinetic data obtained for dogs administered the oral solution, it is clear that absorption is not reliant on the presence of citric acid, when the active constituent is presented in solution.

TABLE 8

Pharmacokinetic parameters

| TREATMENT | $C_{max}$ (ng/ml) | $T_{max}$ (h) | AUC (ng·h/ml) |
|---|---|---|---|
| IVP | 13 | 1.3 | 23 |
| RVP | 17 | 0.7 | 21 |

The observed $C_{max}$ for the IVP treatment group had a mean value of approximately 13 ng/ml and the $T_{max}$ occurred at either 1 or 2 hours. This demonstrates that a solution of pimobendan is rapidly absorbed at a greater rate and to a greater extent than described in the product information for Vetmedin.

Discussion

The objective of the analytical component of this example was to determine the concentration of pimobendan in canine plasma obtained from six adult dogs administered either IVP (oral solution) or RVP (Vetmedin® capsule). The data was required to determine the similarity or difference between IVP and RVP formulations in terms of rate of gastrointestinal absorption of pimobendan, and critical pharmacokinetic parameters $C_{max}$, $T_{max}$ and AUC.

Pimobendan appears to be rapidly absorbed when delivered orally, in solution. Pimobendan concentrations in samples obtained 15 minutes after administration were an average of 4.0 ng/mL (IVP) compared to 1.9 ng/mL (RVP). These results indicate the dissolved pimobendan is bioavailable almost immediately, compared to the solid active constituent delivered in the capsule. Further, the rapid absorption of the solution shows that an intensive, unpalatable amount of citric acid is not required to facilitate drug absorption.

The oral solution presents a broader absorption profile; characterised by a slightly lower $C_{max}$, slightly longer $T_{max}$, and a slightly larger AUC than the RVP based on the three dogs examined in each group. Rates of elimination are comparable between groups, but examination of the data at 3 and 4 hours post-treatment indicates that the average pimobendan concentrations of the IVP group are significantly higher than the average of the RVP group. The solution, on average, has achieved an overall higher systemic concentration of pimobendan, for a longer period. This could translate to an improved therapeutic outcome for dogs receiving the solution.

Conclusions

This project involved analysis of forty-eight canine plasma samples for pimobendan. The samples were representative of six dogs, three each treated with either IVP (solution) or RVP (Vetmedin® capsule). Plasma samples were collected at designated time points following product administration.

An LCMS/MS assay was developed and validated, capable of determining pimobendan in plasma in the range 0.5-50 ng/mL.

Analysis of the data generated indicates that oral administration of the IVP can produce plasma concentrations of pimobendan in the treated dogs that are likely to be therapeutic.

The rapid uptake of pimobendan is evident following administration of the oral solution. The data generated suggest that in the elimination phase, the systemic concentration of pimobendan from the oral solution is slightly higher, and is retained slightly longer than the RVP.

Example 3

Bioavailability Study

The study involved 24 healthy adult Beagles of either gender, including neutered animals, weighing 11.3-21.7 kg, aged between 1 year 9 months and 5 years. Trial dogs were clinically examined and weighed on Day −2. Dogs were ranked on descending order of bodyweight and sequentially blocked into 3 blocks of 8 animals. Animals within each block were randomly allocated (via "draw from a hat") to the 8 treatment groups (1-8) such that each group had a similar range of bodyweights.

Investigational and Control Products
Investigational Veterinary Products (IVP)

IVP 1:

| | |
|---|---|
| Pimobendan | 0.25 g |
| Propylene glycol | 23 ml |
| PEG 300 | 10 ml |
| PVP | 0.3 g |
| Stevioside 90% powder | 0.1 g |
| Acesulfame potassium | 0.1 g |
| Benzyl alcohol | 0.05 ml |
| Glycerol | to 50 ml |

IVP 2:

| | |
|---|---|
| Pimobendan | 0.25 g |
| PEG 300 | 10 g |
| Stevioside 90% powder | 0.30 g |
| Glycerol | 6.0 g |
| Polyvinyl pyrrolidone (PVP) K90 | 0.3 g |
| Benzyl alcohol | 0.05 g |
| Glycerol | to 50 ml |

IVP 3:

| | |
|---|---|
| Benazepril Hydrochloride | 0.25 g |
| Propylene glycol | 23 ml |
| PEG 300 | 10 ml |
| PVP | 0.3 g |
| Stevioside 90% powder | 0.1 g |
| Acesulfame potassium | 0.1 g |
| Benzyl alcohol | 0.05 ml |
| Glycerol | to 50 ml |

IVP 4:

| | |
|---|---|
| Pimobendan | 0.25 g |
| Benazepril Hydrochloride | 0.25 g |
| Propylene glycol | 23 ml |
| PEG 300 | 10 ml |
| PVP | 0.3 g |
| Stevioside 90% powder | 0.1 g |
| Acesulfame potassium | 0.1 g |
| Benzyl alcohol | 0.05 ml |
| Glycerol | to 50 ml |

IVP 5:

| | |
|---|---|
| Pimobendan | 0.25 g |
| Enalapril Maleate | 0.25 g |
| Propylene glycol | 23 ml |
| PEG 300 | 10 ml |
| PVP | 0.3 g |
| Stevioside 90% powder | 0.1 g |
| Acesulfame potassium | 0.1 g |
| Benzyl alcohol | 0.05 ml |
| Glycerol | to 50 ml |

IVP 1 was prepared according to the following protocol:
Step 1 Dissolve pimobendan in propylene glycol (15 ml) while heating to about 65° C.
Step 2 Add glycerol (5 ml) with stirring.
Step 3 Add benzyl alcohol with stirring.
Step 4 Add Polyethylene glycol 300 with stirring.
Step 5 In a separate vessel, dissolve stevioside 90% powder and acesulfame potassium in propylene glycol (5 ml) with stirring.
Step 6 Transfer solution prepared in Step 5 to bulk solution prepared in Step 4 with stirring.
Step 7 In a separate vessel disperse and dissolve polyvinylpyrrolidone K90 powder in propylene glycol (3 ml) and glycerol (3 ml). Heat solution to about 65° C. prior to addition to the bulk.
Step 8 Combine solution prepared in Step 6 with the bulk. Mix until clear. Allow to cool.
Step 9 Add glycerol to final batch volume.

IVP 2 was formulation according to the following protocol:
Step 1. Dissolve pimobendan in PEG300 at 65° C. (approx. 30 min).
Step 2. Add stevioside 90% powder to mixture and dissolve.
Step 3. In a separate vessel, combine glycerol (6.0 g) and polyvinyl pyrrolidone (PVP) K90 (at 65° C.)
Step 4. Add mixture prepared in Step 3 to the dissolved pimobendan.
Step 5. Add benzyl alcohol.
Step 6. Make to 50 mL with glycerol. Mix well.

IVPs 3, 4 and 5 were formulated according to a similar procedure as outlined for IVP1 substituting as required the ingredients listed above.

Control Veterinary Products (CVP)
CVP 1:
Product Name: Vetmedin [1.25 mg, 2.5 mg, 5 mg] Capsules for Dogs
Active agent: Pimobendan
CVP 2:
Product Name: Fortekor 2.5 mg/5 mg Tablets for Dogs and Cats
Active agent: Benazepril Hydrochloride
CVP 3:
Product Name: Enalfor 2.5 mg [5 mg; 10 mg] (Enalapril Maleate) Tablets for Dogs
Active agent: Enalapril Maleate Treatment and Sample Collection This Example describes a single period pharmacokinetic study conducted in dogs administered various cardiovascular agents. Concentrations of pimobendan; benazepril and its active metabolite benazeprilat; enalapril and its active metabolite enalaprilat; were determined in plasma samples collected from test subjects in the hours following administration of the formulations as discussed above.

Dogs were fasted from approximately 0730 on the day prior to treatment which was administered at 0930 (Day 0) or 1000 (Day 1) and consisted of a single dose of the IVP or RVP administered per os to the dogs at 2 minute intervals. Study animals in Treatment Groups 1, 2, 4 & 6 were treated once on Day 0; Groups 3, 5, 7 & 8 once on Day 1. Treatment group 1 was dosed with a solution of Pimobendan 0.5% (IVP1). Treatment group 2 was dosed with a solution of Pimobendan 0.5% (IVP2). Treatment group 3 was dosed with a solution of Benazepril 0.5% (IVP3). Treatment group 4 was dosed with a solution of Pimobendan 0.5% & Benazepril 0.5% (IVP4). Treatment group 5 was dosed with a solution of Pimobendan 0.5% & Enalapril 1.0% (IVP5). Treatment group 6 was dosed with a capsule containing pimobendan (CVP1). Treatment group 7 a tablet containing benazepril hydrochloride (CVP2). Treatment group 8 was dosed with a tablet containing enalapril maleate (CVP3). Immediately after tablet or capsule administration each dog was given a small bolus of water (5-10 mL) by syringe to ensure the tablets reached the stomach and were not potentially sequestered in a 'dry' oesophagus. Liquid formulations were administered using 1.0 mL syringes. Water was available ad libitum. Dogs were held individually in pens for 3 hours post treatment then housed in treatment groups of 3 dogs per pen. No food was allowed for at least 4 hours post-treatment.

Blood samples were collected prior to treatment on Day −2, and 15 min, 30 min, 60 min, 90 min, 2 hr, 3 hr, 4 hr, 8 hr, 12 hr and 24 hr post treatment. Blood samples (approximately 5 mL) were collected from dogs by venipuncture of the Cephalic or Jugular veins using fresh sterile needles and eccentric luer syringes and directly injected into a single 8 mL Vacuette® containing lithium heparin and a gel separator. Samples were centrifuged and plasma collected using fresh disposable plastic pipettes.

Pimobendan concentrations in plasma were determined using a validated analytical method based on instrumental determination using Ultra High Performance Liquid Chromatography—tandem mass spectrometry. Sample preparation involved a deproteination step prior to instrumental determination.

Benazepril, benazeprilat, enalapril and enalaprilat were determined using an analytical method based on instrumental determination using Ultra High Performance Liquid Chromatography—tandem mass spectrometry. The low detection limits were achieved using solid phase extraction for sample preparation.

Matrix-matched calibration curves, prepared using the ratio of analyte to deuterated internal standards, were used for analyte quantitation. Calibration curve correlation coefficients exceeded 0.99 for quantitative runs. The Lower Limits of Quantitation (LLOQ) for pimobendan, benazepril, benazeprilat, enalapril and enalaprilat were determined to be 0.2 ng/mL, deemed sufficient for this study.

Results

TABLE 9

Overall summary of the pharmacokinetics (PK) study for pimobendan, enalapril, enalaprilat, benazepril, and benazeprilat bioavailability

| Group | Analyte | Description | Tmax h | Cmax ng/ml | AUC$_{0-x\ h}$ ng · h/ml | x |
|---|---|---|---|---|---|---|
| Group 7 | Benazepril | CVP2 | 0.58 | 9.91 | 5.55 | 3 h |
| Group 3 | Benazepril | IVP3 | 0.50 | 6.04 | 3.17 | 3 h |
| Group 4 | Benazepril | IVP4 | 0.42 | 24.73 | 16.94 | 3 h |
| Group 3 | Benazeprilat | IVP3 | 2.00 | 31.17 | 130.04 | 24 h |
| Group 7 | Benazeprilat | CVP2 | 2.33 | 11.33 | 91.67 | 24 h |
| Group 4 | Benazeprilat | IVP4 | 1.67 | 24.55 | 113.99 | 24 h |
| Group 8 | Enalapril | CVP3 | 1.50 | 25.50 | 58.01 | 24 h |
| Group 5 | Enalapril | IVP5 | 0.50 | 11.99 | 29.25 | 24 h |
| Group 8 | Enalaprilat | CVP3 | 3.00 | 80.37 | 578.55 | 24 h |
| Group 5 | Enalaprilat | IVP5 | 3.67 | 38.63 | 328.78 | 24 h |
| Group 6 | Pimobendan | CVP1 | 1.42 | 8.13 | 12.66 | 4 h |
| Group 1 | Pimobendan | IVP1 | 0.50 | 25.40 | 32.00 | 4 h |
| Group 2 | Pimobendan | IVP2 | 0.83 | 10.57 | 21.04 | 4 h |
| Group 4 | Pimobendan | IVP4 | 0.58 | 14.70 | 21.58 | 4 h |
| Group 5 | Pimobendan | IVP5 | 0.42 | 12.73 | 14.31 | 4 h |

Discussion

Pimobendan Pharmacokinetics (PK)

Groups 1, 2, 4, 5 and 6 were administered compositions comprising pimobendan, i.e. IVPs 1, 2, 4 and 5 and CVP1, respectively. All animals in groups 1, 2, 4, 5 and 6 were administered pimobendan at a target dose rate of 0.25 mg/kg.

TABLE 10

Pimobendan pharmacokinetics over a 24 hour period post-dosing

| Group | IVP/CVP | 0 | 0.25 | 0.5 | 1 | 1.5 | 2 | 3 | 4 | 8 | 12 | 24 |
|---|---|---|---|---|---|---|---|---|---|---|---|---|
| 1 | IVP 1 | 0.00 | 14.56 | 25.40 | 14.44 | 9.57 | 5.52 | 2.22 | 0.94 | 0.05 | 0.05 | 0.05 |
| 2 | IVP 2 | 0.00 | 5.58 | 9.86 | 9.08 | 7.40 | 5.67 | 3.55 | 1.44 | 0.05 | 0.05 | 0.05 |
| 6 | CVP1 | 0.00 | 4.32 | 3.76 | 4.87 | 4.00 | 3.28 | 2.69 | 1.18 | 0.05 | 0.05 | 0.05 |
| 4 | IVP4 | 0.00 | 12.24 | 13.97 | 8.62 | 6.38 | 4.22 | 2.05 | 1.12 | 0.05 | 0.05 | 0.05 |
| 5 | IVP5 | 0.00 | 10.00 | 11.78 | 5.71 | 3.63 | 2.11 | 0.85 | 0.36 | 0.05 | 0.05 | 0.05 |

TABLE 11

Summary of pimobendan PK results

| Group | Description | Tmax h | Cmax ng/ml | AUC0-4 h ng · h/ml |
|---|---|---|---|---|
| Group 1 | IVP1 | 0.50 | 25.40 | 32.00 |
| Group 2 | IVP2 | 0.83 | 10.57 | 21.04 |
| Group 4 | IVP4 | 0.58 | 14.70 | 21.58 |
| Group 5 | IVP5 | 0.42 | 12.73 | 14.31 |
| Group 6 | CVP1 | 1.42 | 8.13 | 12.66 |

Figure 2:
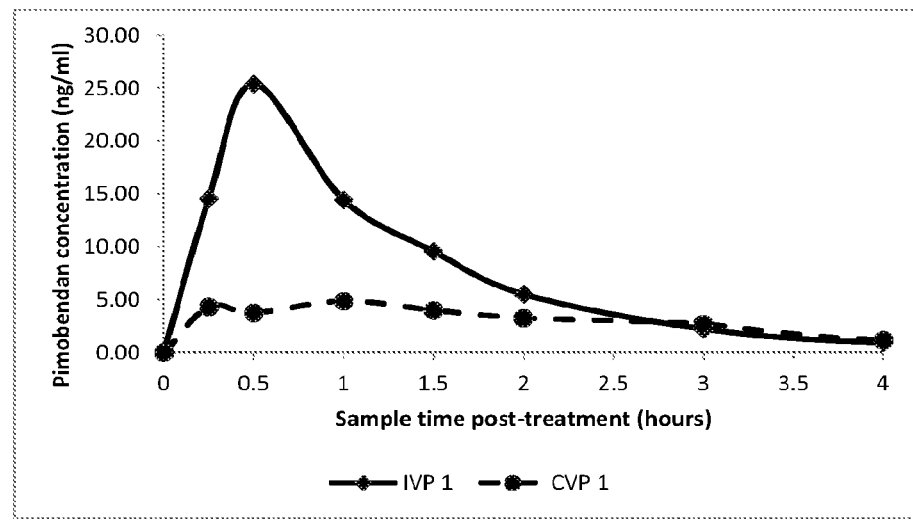
FIG. 2 is a graph which shows a similar comparison as in FIG. 1 with another IVP compared to a Commercial Veterinary Product (CVP) containing pimobendan, from a separate in vivo trial.

All treatment groups showed bioavailability of pimobendan after administration. IVP 1, comprising pimobendan and propylene glycol, demonstrated higher AUC than the commercial veterinary product, Vetmedin, a solid formulation comprising pimobendan and citric acid (FIG. 2). These results showed decreased AUC for Vetmedin compared with the earlier trial discussed in Example 2 above, most likely due to natural biological variation.

IVP1, i.e. comprising pimobendan and propylene glycol, also demonstrated greater AUC than IVP 2, i.e. comprising pimobendan and excluding propylene glycol. IVP 2 contains both PEG300 and glycerol and these results suggest that propylene glycol is more effective at providing increased bioavailability of pimobendan after oral administration than a liquid formulation comprising solvents capable of solubilising pimobendan that are structurally similar to propylene glycol, i.e. PEG300 and glycerol (FIG. 3).

Figure 4:
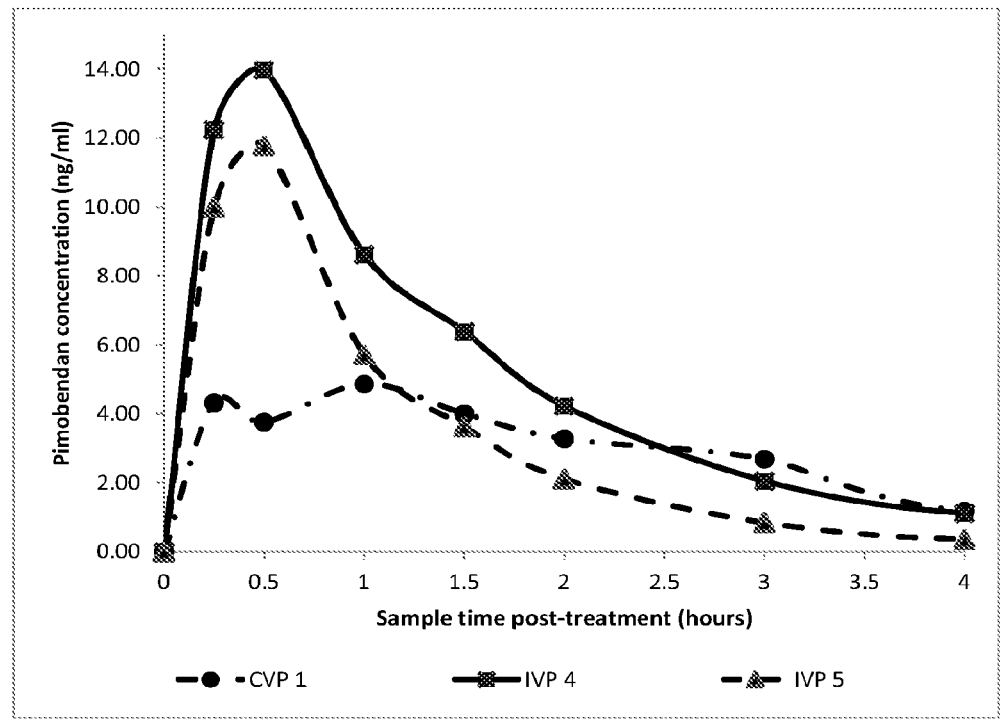
FIG. 4 is a graph which shows a comparison between plasma pimobendan concentrations in dogs after oral administration of two Investigational Veterinary Products containing a combination of pimobendan and an ACE-I and a Commercial Veterinary Product CVP containing pimobendan as the active ingredient.
Figure 5:
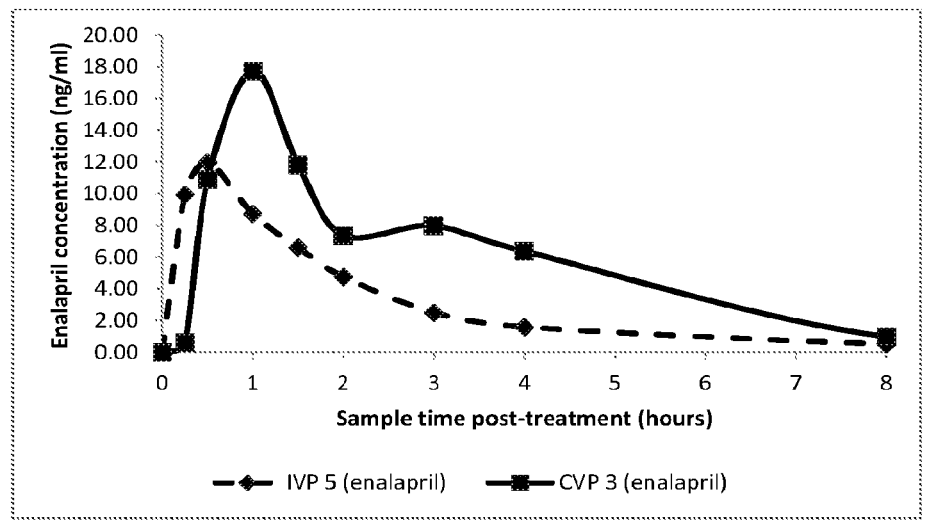
FIG. 5 is a graph which shows a comparison between plasma enalapril concentrations in dogs after oral administration of an Investigational Veterinary Product (IVP) containing pimobendan and enalapril and a Commercial Veterinary Product (CVP) containing enalapril without pimobendan.
Figure 6:
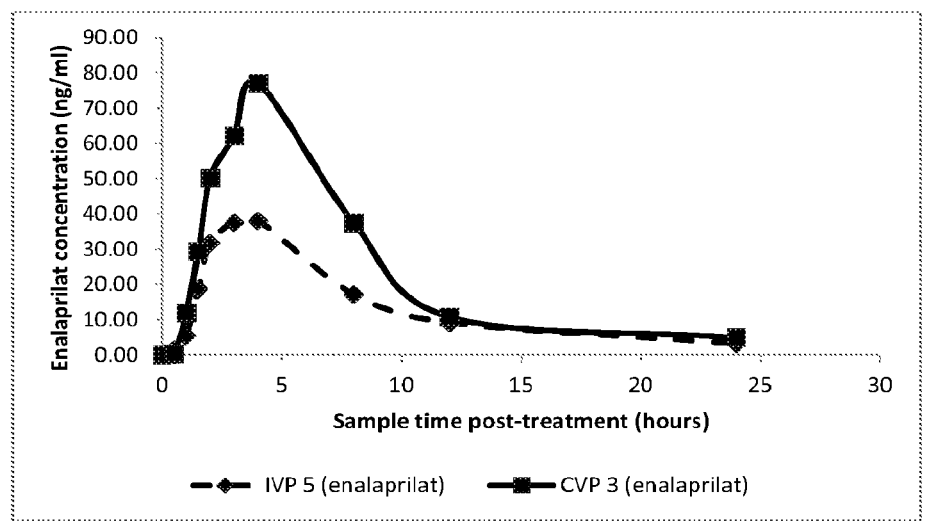
FIG. 6 is a graph which shows a comparison between plasma enalaprilat concentrations in dogs after oral administration of the IVP and CVP of FIG. 5.

IVPs 4 and 5 both comprise a combination of pimobendan and an ACE-I. Both are shown to provide an AUC within the therapeutic range and greater than CVP1 (FIG. 4). IVPs 4 and 5, however, displayed a lower AUC than IVP1 suggesting that the presence of ACE-I may affect the bioabsorption of the pimobendan. However, as mentioned above, the AUC, Cmax and Tmax of pimobendan measured after oral administration of IVPs 4 and 5 are suitable for use in therapy in the methods described herein. Further, the increased effectiveness of propylene glycol compared to other solvents, e.g. PEG300 and glycerol, is particularly useful in these combination formulations to provide desirable plasma concentrations for pimobendan after oral administration.

Enalapril PK

Enalapril is an orally available prodrug of the active agent enalaprilat. The plasma concentrations of enalapril and enalaprilat were measured. The concentration of enalaprilat relates to the effectiveness of this ACE-I dosage.

TABLE 12

Enalapril and enalaprilat pharmacokinetics over a 24 hour period post dosing

| Group | IVP/CVP | 0 | 0.25 | 0.5 | 1 | 1.5 | 2 | 3 | 4 | 8 | 12 | 24 |
|---|---|---|---|---|---|---|---|---|---|---|---|---|
| 5 | IVP5 (Enalapril) | 0.00 | 9.94 | 11.99 | 8.72 | 6.61 | 4.76 | 2.51 | 1.60 | 0.53 | 0.26 | 0.05 |
| 8 | CVP3 (Enalapril) | 0.00 | 0.62 | 10.89 | 17.73 | 11.81 | 7.38 | 7.98 | 6.37 | 0.98 | 0.57 | 0.17 |
| 5 | IVP5 (Enalaprilat) | 0.00 | 0.20 | 1.45 | 5.35 | 18.71 | 31.71 | 37.50 | 37.97 | 17.10 | 9.05 | 3.19 |
| 8 | CVP3 (Enalaprilat) | 0.00 | 0.05 | 0.38 | 11.99 | 29.34 | 50.15 | 62.19 | 77.03 | 37.43 | 10.77 | 4.92 |

TABLE 13

Summary of enalapril PK results

| Group | Analyte | Description | Tmax h | Cmax ng/ml | AUC$_{0-x\,h}$ ng·h/ml | x |
|---|---|---|---|---|---|---|
| Group 8 | Enalapril | CVP3 | 1.50 | 25.50 | 58.01 | 24 h |
| Group 5 | Enalapril | IVP5 | 0.50 | 11.99 | 29.25 | 24 h |

TABLE 14

Summary of enalaprilat PK results

| Group | Analyte | Description | Tmax h | Cmax ng/ml | AUC$_{0-x\,h}$ ng·h/ml | x |
|---|---|---|---|---|---|---|
| Group 8 | Enalaprilat | CVP3 | 3.00 | 80.37 | 578.55 | 24 h |
| Group 5 | Enalaprilat | IVP5 | 3.67 | 38.63 | 328.78 | 24 h |

Figure 7:
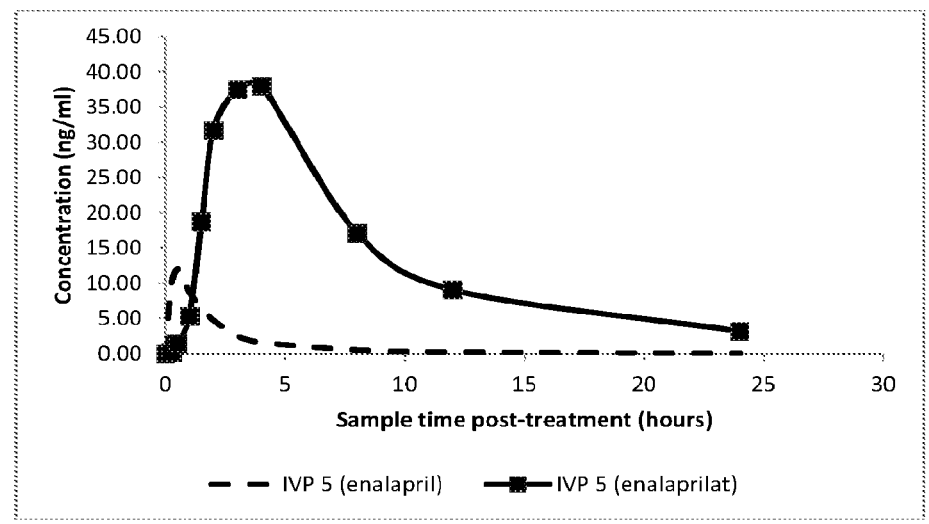
FIG. 7 is a graph which shows the plasma concentrations of enalapril and enalaprilat after oral administration of the IVP of FIGS. 5 and 6 demonstrating the in vivo conversion of the prodrug enalapril to the active enalaprilat.
Figure 8:
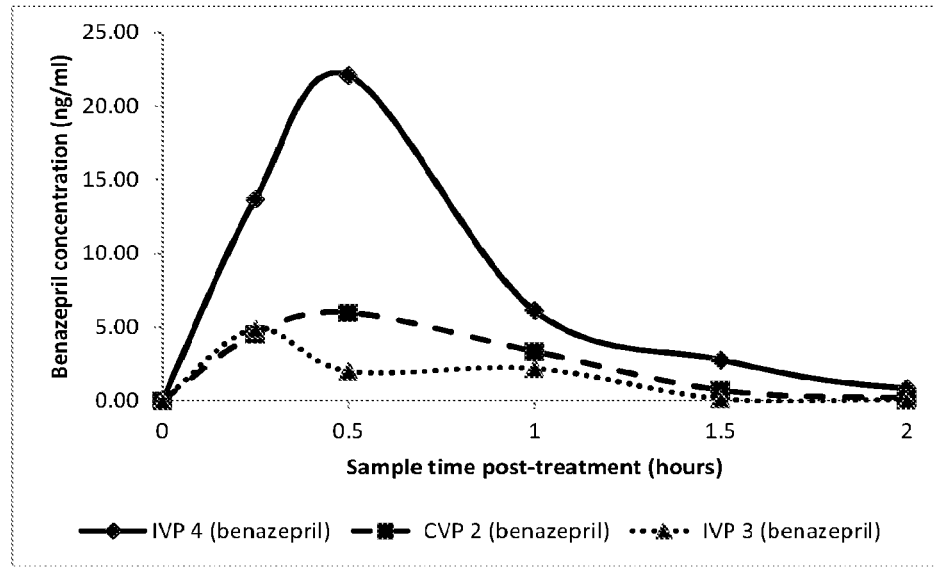
FIG. 8 is a graph which shows a comparison of plasma benazepril concentrations in IVP4 containing a combination of pimobendan and benazepril, an IVP3 containing benazepril without pimobendan and a Commercial Veterinary Product (CVP2) containing benazepril without pimobendan.
Figure 9:
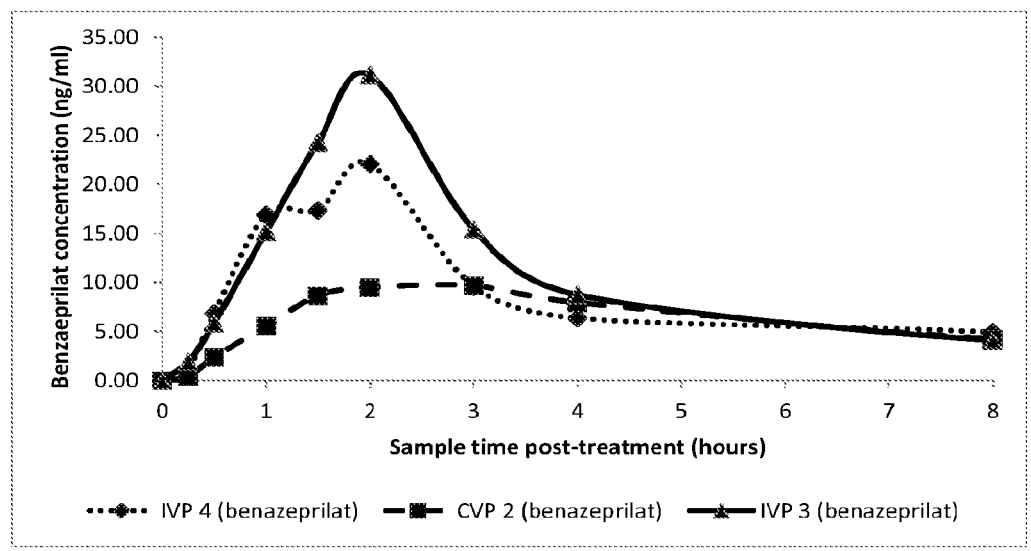
FIG. 9 is a graph which shows a comparison of plasma benazeprilat concentrations of IVP4, IVP3 and CVP2 as described for FIG. 8.

As shown in FIG. 7 the enalaprilat concentration increases as the enalapril concentration decreases. This relationship is due to the conversion in vivo of enalapril to enalaprilat.

Although these data show a greater AUC for enalaprilat following administration of CVP3 than IVP5, the AUC for IVP5 is in line with the published AUC for enalaprilat following 0.5 mg/kg dose of enalapril. The published AUC for enalaprilat following administration of enalapril at 0.5 mg/kg to dogs is 393 ng/h/ml (=23,589 ng/m in/ml) (see, for example, Toutain, P. L., H. P. Lefebvre, and V. Laroute. 2000. New insights on effect of kidney insufficiency on disposition of angiotensin converting enzyme inhibitors: case of enalapril and benazepril in dogs. *J Pharmacol Exp Ther* 292:1094-103).

Benazepril PK

As discussed above for enalapril, benazepril is a prodrug of the active benazeprilat. Thus, the concentration of benazeprilat relates to the effective ACE-I dose for each formulation.

TABLE 15

Benazepril and benazeprilat pharmacokinetics over a 24 hour period post dosing

| Group | IVP/CVP (Analyte) | 0 | 0.25 | 0.5 | 1 | 1.5 | 2 | 3 | 4 | 8 | 12 | 24 |
|---|---|---|---|---|---|---|---|---|---|---|---|---|
| 3 | IVP3 (Benazepril) | 0.00 | 4.85 | 2.00 | 2.17 | 0.13 | 0.05 | 0.05 | 0.05 | 0.05 | 0.05 | 0.05 |
| 4 | IVP4 (Benazepril) | 0.00 | 13.7 | 22.1 | 6.11 | 2.76 | 0.85 | 0.33 | 0.11 | 0.05 | 0.05 | 0.05 |
| 7 | CVP2 (Benazepril) | 0.00 | 4.51 | 6.0 | 3.33 | 0.72 | 0.18 | 0.05 | 0.05 | 0.05 | 0.05 | 0.05 |
| 3 | IVP3 (Benazeprilat) | 0.00 | 1.92 | 5.87 | 15.2 | 24.3 | 31.2 | 15.4 | 8.75 | 4.10 | 2.71 | 1.48 |
| 4 | IVP4 (Benazeprilat) | 0.00 | 1.09 | 6.86 | 16.9 | 17.4 | 22.1 | 9.58 | 6.36 | 4.93 | 2.26 | 2.36 |
| 7 | CVP2 (Benazeprilat) | 0.00 | 0.40 | 2.39 | 5.55 | 8.65 | 9.47 | 9.68 | 7.95 | 4.23 | 2.65 | 1.47 |

TABLE 16

Summary of benazepril PK results

| Group | Analyte | Description | Tmax h | Cmax ng/ml | AUC$_{0-x\,h}$ ng·h/ml | x |
|---|---|---|---|---|---|---|
| Group 7 | Benazepril | CVP2 | 0.58 | 9.91 | 5.55 | 3 h |
| Group 3 | Benazepril | IVP3 | 0.50 | 6.04 | 3.17 | 3 h |
| Group 4 | Benazepril | IVP4 | 0.42 | 24.73 | 16.94 | 3 h |

TABLE 17

Summary of benazeprilat PK results

| Group | Analyte | Description | Tmax h | Cmax ng/ml | AUC$_{0-x\,h}$ ng·h/ml | x |
|---|---|---|---|---|---|---|
| Group 7 | Benazeprilat | CVP2 | 2.33 | 11.33 | 91.67 | 24 h |
| Group 3 | Benazeprilat | IVP3 | 2.00 | 31.17 | 130.04 | 24 h |
| Group 4 | Benazeprilat | IVP4 | 1.67 | 24.55 | 113.99 | 24 h |

Figure 10:
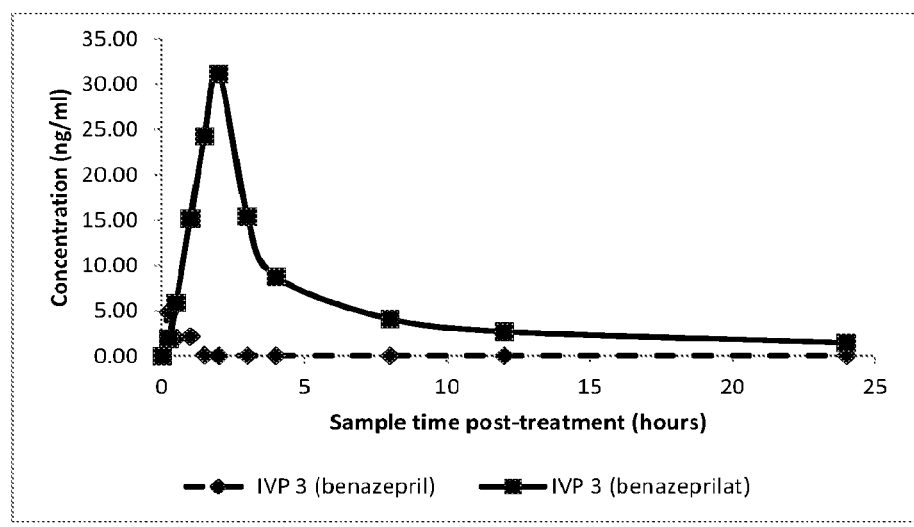
FIG. 10 is a graph which shows plasma concentrations of benazepril and benazeprilat after oral administration of IVP3 demonstrating the in vivo conversion of the prodrug benazepril to the active benazeprilat.
Figure 11:
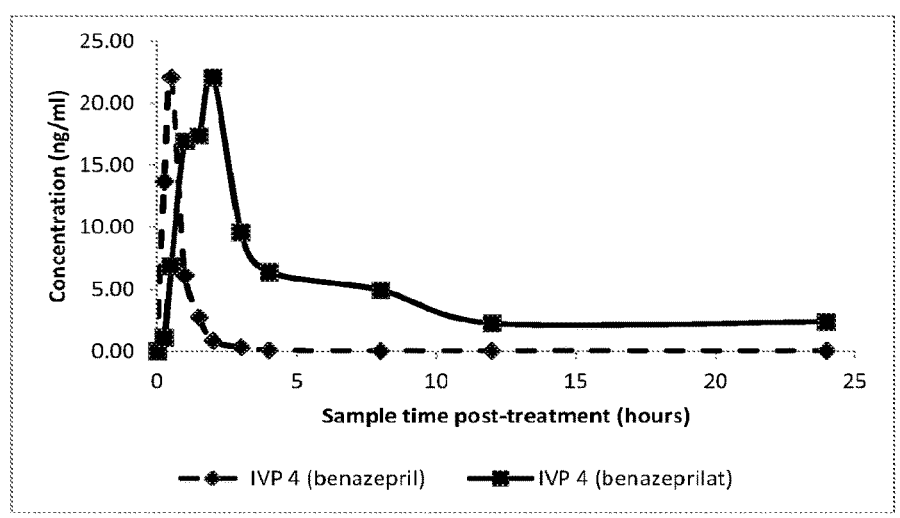
FIG. 11 is a graph which shows plasma concentrations of benazepril and benazeprilat after oral administration of IVP4 demonstrating the in vivo conversion of the prodrug benazepril to the active benazeprilat.

As shown in FIGS. 10 and 11 the benazeprilat concentration increases as the benazepril is converted to benazeprilat in vivo.

Administration of IVPs 3 and 4 both resulted in a higher AUC of the active benazeprilat than CVP 2. The published AUC for benazeprilat following administration of benazepril at 0.5 mg/kg to dogs is 230 ng/h/ml (=13.790 ng/min/ml)=114.9 ng/h/ml for a dose of 0.25 mg/kg (see for example Toutain, P. L., H. P. Lefebvre, and V. Laroute. 2000. New insights on effect of kidney insufficiency on disposition of angiotensin converting enzyme inhibitors: case of enalapril and benazepril in dogs. *J Pharmacol Exp Ther* 292: 1094-103). The results for both IVPs 3 and 4 are consistent with this value.

IVP 3 comprises benazepril only and IVP 4 comprises benazepril and pimobendan as active ingredients. The AUC of benazeprilat is greater for IVP3 than IVP4. The benazepril concentration following administration of IVP 4 has a higher Cmax and AUC in the first 3 hours than for IVP 3, which may have contributed to the lower AUC of benazeprilat for IVP 4.

Conclusions

These results demonstrate that a liquid formulation comprising pimobendan and propylene glycol effectively administers pimobendan to an animal after oral administration. Further, these results indicate the unexpected efficacy of propylene glycol as the Cmax and AUC of IVP1 greatly exceeds that of the similar IVP2 absent propylene glycol. Also, the results demonstrate that a liquid formulation comprising a combination of pimobendan and either enalapril or benazepril with propylene glycol provides orally bioavailable amounts of both active agents. Further, a liquid formulation comprising benazepril and propylene glycol provide bioavailable benazeprilat in dogs following oral administration.

It is to be understood that a reference herein to a prior art document does not constitute an admission that the document forms part of the common general knowledge in the art in Australia or in any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The claims defining the invention are as follows:

1. A stable orally bioavailable non-aqueous liquid formulation comprising between 7 wt % and 65 WT % of the total formulation of propylene glycol and an effective amount of an angiotensin converting enzyme inhibitor selected from the group consisting of enalapril and benazepril and pharmaceutically and veterinary acceptable salts thereof.

2. The liquid formulation of claim 1, wherein the angiotensin converting enzyme inhibitor is present in an amount of about 0.1 wt % to about 50 wt % of the total formulation.

3. The liquid formulation of claim 1, further comprising one or more additional active agents and wherein the additional active agent is a diuretic.

4. The liquid formulation of claim 3, wherein the diuretic is selected from the group consisting of furosemide, hydrochlorothiazide, chlorthalidone, bumetanide, ethacrynic acid, torasemide, chlorothiazide, spironolactone, triamterene, amiloride and pharmaceutically or veterinary salts thereof, or a combination thereof.

5. The liquid formulation of claim 3, wherein the one or more additional active agents is present in an amount of about 0.1 wt % to about 50 wt % of the total formulation.

6. The liquid formulation of claim 1 which is a veterinary formulation.

7. A method of treating cardiac disease and/or hypertension in a non-human subject, comprising administering an effective amount of the liquid formulation of claim 1 to a subject in need thereof.

8. The method of claim 7, wherein cardiac disease is a primary heart disease selected from the group consisting of congestive heart failure (CHF), acute CHF, chronic CHF, decompensated endocardiosis (DCE), dilated cardiomyopathy (DCM), asymptomatic (occult) CHF, asymptomatic DCM, and chronic valvular heart disease, or a combination thereof.

9. The method of claim 7, wherein cardiac disease is a secondary heart disease and is selected from the group consisting of cardiovascular dysfunction and impaired renal perfusion during anaesthesia, shock, gastric dilation, volvulus, myocardial ischaemia, and renal ischaemia, or a combination thereof.

10. A process for the preparation of the liquid formulation of claim 1 which comprises mixing an effective amount of an angiotensin converting enzyme inhibitor selected from the group consisting of enalapril and benazepril, and pharmaceutically and veterinary acceptable salts thereof with between 7 wt % and 65 WT % of the total formulation of propylene glycol.

11. A kit comprising a first formulation comprising: an effective amount of an angiotensin converting enzyme inhibitor selected from the group consisting of enalapril and benazepril, and pharmaceutically and veterinary acceptable salts thereof and a second formulation comprising a further active agent, wherein the first and second formulations are held separately and the first formulation comprises between 7 wt % and 65 WT % of the total formulation of propylene glycol.

* * * * *